(12) United States Patent
Abrams et al.

(10) Patent No.: US 12,082,908 B2
(45) Date of Patent: Sep. 10, 2024

(54) DEVICES AND METHODS FOR THE INTRA-OPERATIVE VERIFICATION OF ORAL HEALTH PROCEDURES

(71) Applicant: QUANTUM DENTAL TECHNOLOGIES INC., Toronto (CA)

(72) Inventors: Stephen Abrams, Toronto (CA); Koneswaran Sivagurunathan, Scarborough (CA)

(*) Notice: Subject to any disclaimer, the term of this patent is extended or adjusted under 35 U.S.C. 154(b) by 712 days.

(21) Appl. No.: 17/416,665

(22) PCT Filed: Dec. 21, 2019

(86) PCT No.: PCT/CA2019/051868
§ 371 (c)(1),
(2) Date: Jun. 21, 2021

(87) PCT Pub. No.: WO2020/124250
PCT Pub. Date: Jun. 25, 2020

(65) Prior Publication Data
US 2022/0039660 A1 Feb. 10, 2022

Related U.S. Application Data

(60) Provisional application No. 62/784,173, filed on Dec. 21, 2018.

(51) Int. Cl.
*A61B 5/00* (2006.01)
*A61C 5/40* (2017.01)
*A61C 19/04* (2006.01)

(52) U.S. Cl.
CPC .......... *A61B 5/0088* (2013.01); *A61B 5/0035* (2013.01); *A61B 5/0093* (2013.01);
(Continued)

(58) Field of Classification Search
CPC ... A61B 5/0088; A61B 5/0035; A61B 5/0093; A61B 5/4547; A61B 2560/0425;
(Continued)

(56) References Cited

U.S. PATENT DOCUMENTS 5,503,559 A 4/1996 Vari
6,584,341 B1 6/2003 Mandelis et al.
(Continued)

OTHER PUBLICATIONS

Ho, Q. et al, "Laser Fluorescence Assessment of the Root Canal Using Plain and Conical Optical Fibers", J. Endodontics 36, 119-122 (2010).
(Continued)

*Primary Examiner* — Md M Rahman
(74) *Attorney, Agent, or Firm* — HILL & SCHUMACHER

(57) ABSTRACT

An intraoral optical probe is provided that includes a distal elongate optical waveguide for interrogating dental tissue. In some example embodiments, the elongate optical waveguide has dimensions suitable for the insertion of the waveguide into an exposed root canal. According to various example embodiments, the elongate optical waveguide, when inserted into an internal region of a tooth, can direct incident optical radiation from the intraoral optical probe directly onto an inner surface, such as an internal surface of a root canal, such that status of the root canal can be interrogated directly. The intraoral optical probe may be employed to provide intraoperative feedback regarding internal dental tissue, such as interoperative feedback pertaining to the interior of the root canal during an endodontic procedure, location of secondary or lateral root canals, location of the apex or tip of the root canal system and or detection of the pulp chamber roof or floor.

20 Claims, 29 Drawing Sheets

(52) U.S. Cl.
CPC ............ *A61B 5/4547* (2013.01); *A61C 19/04* (2013.01); *A61C 19/042* (2013.01); *A61B 2560/0425* (2013.01); *A61B 2562/0238* (2013.01); *A61B 2576/02* (2013.01); *A61C 5/40* (2017.02)

(58) Field of Classification Search
CPC ........ A61B 2562/0238; A61B 2576/02; A61C 19/04; A61C 19/042; A61C 5/40
USPC .......................................................... 356/73
See application file for complete search history.

(56) References Cited

U.S. PATENT DOCUMENTS

| | | | |
|---|---|---|---|
| 7,331,954 | B2 | 2/2008 | Temelkuran et al. |
| 7,421,186 | B2 | 9/2008 | Boutoussov et al. |
| 8,977,085 | B2 | 3/2015 | Walsh et al. |
| 2007/0021670 | A1 | 1/2007 | Mandelis et al. |
| 2007/0188738 | A1 | 8/2007 | Jung et al. |
| 2008/0219629 | A1 | 9/2008 | Rizoiu et al. |
| 2010/0221677 | A1 | 9/2010 | Hennig |
| 2010/0227296 | A1 | 9/2010 | Mandelis et al. |
| 2013/0141558 | A1 | 6/2013 | Jeon et al. |
| 2013/0177865 | A1 | 7/2013 | Ostler |
| 2015/0346095 | A1 | 12/2015 | Jeon et al. |

OTHER PUBLICATIONS

Jeon, R J. et al., "Detection of interproximal demineralized lesions on human teeth in vitro using frequency-domain infrared photothermal radiometry and modulated luminescence", Journal of Biomedical Optics, vol. 12, Issue 3, pp. 1-13, May 1, 2007 (Jan. 5, 2007).

International Search Report for PCT/CA2019/051868 dated Mar. 30, 2020.

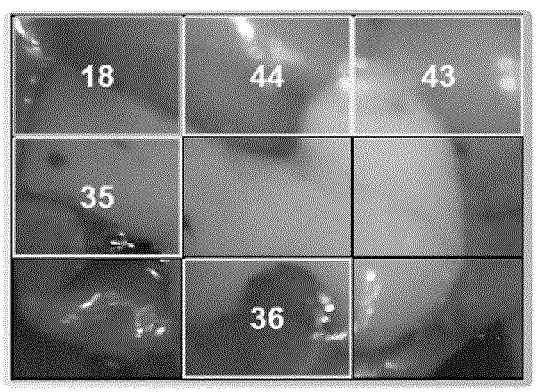
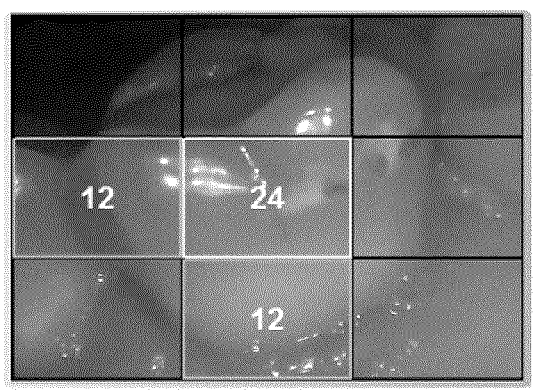
FIG. 1B                    FIG. 1C

☐ Test 1: Initial testing of root canal wall status based on the reference values (Ref PTR Amp:A1, Ref PTR Ph:P1) for stronger signal to noise ratio (SNR) of PTR Amplitude (PTR-Amp, PTR-Amp std) and PTR Phase (PTR-Ph, PTR-Ph-std) responses.

Test 1: A:(PTR-Amp)/(PTR-Amp-std) > Ref A1 &
  B: (PTR-Ph)/(PTR-Ph-std) > Ref P1

☐ Test 2: Final confirmation of the status of healthy root canal wall status based on the reference values (Ref PTR Amp:A2, Ref PTR Ph:P2) for weaker SNR of PTR Amplitude (PTR-Amp, PTR-Amp std) and PTR Phase (PTR-Ph, PTR-Ph-std) responses.

Test 2: A: (PTR-Amp)/(PTR-Amp-std) > Ref A2 &
  B: (PTR-Ph)/(PTR-Ph-std) > Ref P2

☐ Test 3: Testing the status of surface debris on the root canal wall based on the reference value (Ref B) changes in LUM phase response.

Test 3: (LUM-Phase shift) < Ref B $$\text{Measurement Error} = \sqrt{\left(\frac{PTR_{Amp}STD}{PTR_{Amp}}\right)^2 + \left(\frac{PTR_{Phase}STD}{PTR_{Phase}}\right)^2 + \left(\frac{LUM_{Amp}STD}{LUM_{Amp}}\right)^2 + \left(\frac{LUM_{Phase}STD}{LUM_{Phase}}\right)^2}$$

FIG. 4E

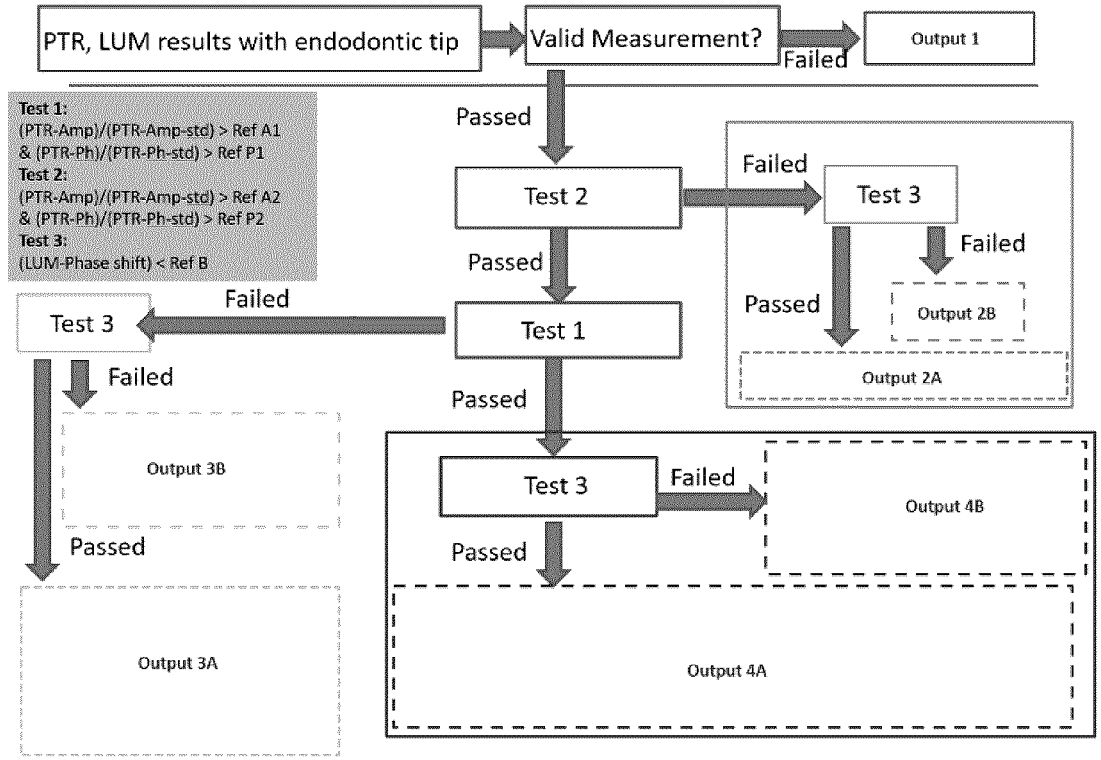

☐ Output #1: → Repeat scan

☐ Output #2A: → Healthy dentin wall. The Cleanest root canal wall with less than 1 degree of backscattered surface LUM drop in Phase (gold standard cleaning).
*Case 4C*

☐ Output #2B: → Healthy dentin wall. Cleaned root canal wall but with a drop (>1 degree) in backscattered surface LUM in Phase from particles on wall.
*Case 3B*

☐ Output #3A: → Early demin/crack in dentin wall of clear surface with less than 1 degree of backscattered surface LUM drop in Phase.
*Case 4B*

☐ Output #3B: → Early demin/carious dentin wall. Mild cleaning needed to remove soft surface debris and to treat early dentin demin/carious wall.
*Case 3A*

☐ Output #4A: → Cracks (permanent on dentin wall or due to drilling the thin top opening of chamber) with clear surface wall.
*Case 5A*

☐ Output #4B: → Defects up to deep surface with demin/caries/cracks as well as soft debris on the wall surface. Extra cleaning needed to remove the debris and to repair hard demin/crack dentin wall crystal structures.
*(Examples: Case 1A,1B,2A)*

FIG. 4F

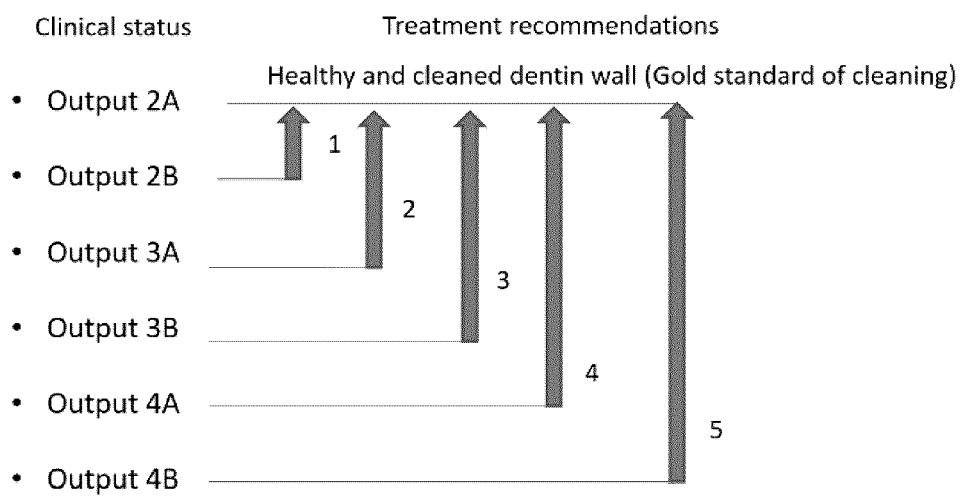

1-Changing output status of 2B to 2A: Remove micron scale particles deposited on the wall.
2-Changing output status of 3A to 2A: Apply remin treatment on the wall.
3-Changing output status of 3B to 2A: Mild cleaning and apply remin treatment on the wall.
4-Changing output status of 4A to 2A: Further drilling and cleaning the wall.
5-Changing output status of 4B to 2A: Advanced cleaning and apply remin treatment on the wall.

FIG. 4G

Case 1

Before Cleaning

Changes in PTR Amp, PTR Phase
LUM Phase Before and After Cleaning

After Cleaning

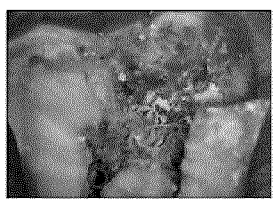 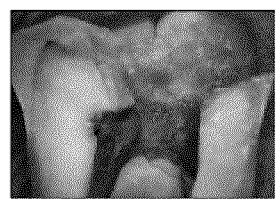

Cleaning results : Before and After

PTR Amp: 395.1 +/- 12.7 to 104.3 +/- 6.1
PTR Phase: 35.7 +/- 1.9 to 33.4 +/- 2.1
LUM Phase: 178.4 +/- 1.0 to 172.3 +/- 4.0

Test 1:
A: (PTR-Amp)/(PTR-Amp-std) > Ref A1 (=5) &
B: (PTR-Ph)/(PTR-Ph-std) > Ref P1 (5)

Test 2:
A: (PTR-Amp)/(PTR-Amp-std) > Ref A2 (=2) &
B: (PTR-Ph)/(PTR-Ph-std) > Ref P2 (=2)

Test 3:
(LUM-Phase shift) < Ref B (=1.0)

Canary endodontic test results on the scanned spot:

FIG. 5A

*Case 1A*
Before Cleaning

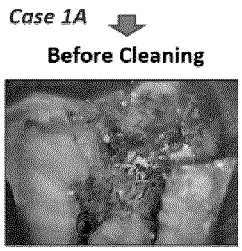

Changes in PTR Amp, PTR Phase LUM Phase Before Cleaning
PTR Amp: 395.1 +/- 12.7
PTR Phase: 35.7 +/- 1.9
LUM Phase: 178.4 +/- 1.0

Output# 4B: if the probing root canal underneath the tip & debris present.

Test 1: A: (PTR-Amp)/(PTR-Amp-std) > Ref A1 &
B: (PTR-Ph)/(PTR-Ph-std) > Ref P1

Test 3: (LUM-Phase shift) < Ref B

Test 1 : Before cleaning: Passed
PTR Amp/PTR-Amp-std = 395.1 / 12.7 = 31.1 > Ref A1(=5) &
PTR Phase/PTR Ph-std = 35.7 / 1.9 = 18.8 > Ref P1 (=5)

Test 3: Before cleaning : Failed.
LUM Phase: 180-178.4=1.6 > Ref B (1.0)

Case 1A: Output #4B
Defects up to deep surface with demin/caries/cracks as well as soft debris on the wall surface. Extra cleaning needed to remove the debris and to repair hard demin/crack dentin wall crystal structures.

As shown in photo, Case 1A results were scanned before cleaning the root canal. The wall was strongly demin as explained with clinical output #4B from the endodontic application with the Canary system.

FIG. 5B

*Case 1B*
After Cleaning

Changes in PTR Amp, PTR Phase LUM Phase After Cleaning
PTR Amp: 104.3 +/- 6.1
PTR Phase: 33.4 +/- 2.1
LUM Phase: 172.3 +/- 4.0

Test 1: A: (PTR-Amp)/(PTR-Amp-std) > Ref A1 &
B: (PTR-Ph)/(PTR-Ph-std) > Ref P1

Output #4B: if the probing root canal beneath the tip is clean of debris but still has advanced demin wall.

Test 3: (LUM-Phase shift) < Ref B

Test 1 : After cleaning: Passed
PTR Amp/PTR-Amp-std = 104.3 / 6.1 = 17 > Ref A1(=5) &
PTR Phase/PTR Ph-std = 33.4 / 2.1 = 15.9 > Ref P1 (=5)

Test 3: After cleaning : Failed.
LUM Phase: 180-172.3=7.7 < Ref B (1.0)

Case 1B: Output #4B
Defects up to deep surface with demin/caries/cracks as well as soft debris on the wall surface. Extra cleaning needed to remove the debris and to repair hard demin/crack dentin wall crystal structures.

Even though Case 1B results were scanned after cleaning the root canal, the wall was still strongly demin and further cleaning needed to remove soft debris on the wall as well as further treatment needed to remin the wall surface.

FIG. 5C

*Case 2*

Before Cleaning

Changes in PTR Amp, PTR Phase
LUM Phase Before and After Cleaning

After Cleaning

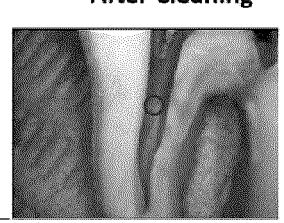

Cleaning results : Before and  After

PTR Amp: 205.6 +/- 7.6 to 12.5 +/- 3.3
PTR Phase: 39.3 +/- 2.4 to 47.2 +/- 26.3
LUM Phase: 143.5 +/- 23.3 to 176.1 +/- 1.5

Test 1:
A: (PTR-Amp)/(PTR-Amp-std) > Ref A1 (=5) &
B: (PTR-Ph)/(PTR-Ph-std) > Ref P1 (5)
Test 2:
A: (PTR-Amp)/(PTR-Amp-std) > Ref A2 (=2) &
B: (PTR-Ph)/(PTR-Ph-std) > Ref P2 (2)

Test 3:
(LUM-Phase shift) < Ref B (=1.0)

Canary endodontic test results on the scanned spot:

FIG. 5D

Case 2A
Before Cleaning

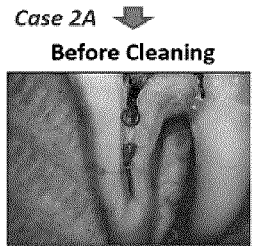

Changes in PTR Amp, PTR Phase
LUM Phase Before Cleaning

PTR Amp: 205.6 +/- 7.6
PTR Phase: 39.3 +/- 2.4
LUM Phase: 143.5 +/- 23.3

Output 4B: if the probing root canal underneath the tip & debris present.

Test 1: (PTR-Amp)/(PTR-Amp-std) > Ref A1 &
(PTR-Ph)/(PTR-Ph-std) > Ref P1

Test 3: (LUM-Phase shift) < Ref B

Test 1 : Before cleaning: Passed
PTR Amp/PTR-Amp-std = 205.6 / 7.6 = 27.1 > Ref A1(=5) &
PTR Phase/PTR Ph-std = 39.3 / 2.4 = 16.4 > Ref P1 (=5)

Test 3: Before cleaning : Failed.
LUM Phase: 180-143.5=36.5 > Ref B (1.0)

Case 2A: Output #4B

Defects up to deep surface with demin/caries/cracks as well as soft debris on the wall surface. Extra cleaning needed to remove the debris and to repair hard demin/crack dentin wall crystal structures.

Case 2A results were scanned before cleaning the root canal, the wall was strongly demin and strong cleaning needed to remove soft debris on the wall.

FIG. 5E

Changes in PTR Amp, PTR Phase
LUM Phase After Cleaning

Case 2B
After Cleaning

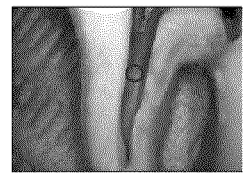

PTR Amp: 12.5 +/- 3.3
PTR Phase: 47.2 +/- 26.3
LUM Phase: 176.1 +/- 1.5

Test 1: A: (PTR-Amp)/(PTR-Amp-std) > Ref A1 &
B: (PTR-Ph)/(PTR-Ph-std) > Ref P1
(Ref A1=5 and Ref P1 =5)
Test 2: A: (PTR-Amp)/(PTR-Amp-std) > Ref A2 &
B: (PTR-Ph)/(PTR-Ph-std) > Ref P2
(Ref A1=2 and Ref P1 =2)
Test 3: (LUM-Phase shift) < Ref B Output 2: if the probing root canal beneath the tip is clean of debris.

Case 2B: Output 2B

Test 1 failed and Test 2 failed: After cleaning:
PTR Amp/PTR-Amp-std = 12.5 / 3.3= 3.8 (< Ref A1 but > Ref A2) &
PTR Phase/PTR Ph-std = 47.2 / 26.3 = 1.8 (< Ref P1 and Ref P2)
Test 3: After cleaning : Failed.
LUM Phase: 180-176.1=3.9 > Ref B (1.0)

Healthy dentin wall. Cleaned root canal wall but with a drop (>1 degree) in backscattered surface LUM in Phase from particles on wall.

As seen on the photo of the scan spot, Case 2B results were scanned after cleaning the root canal, PTR-Amp, PTR Phase in Healthy range. But the surface wall still had micro scale particles deposited on the wall (due to failed Test 3). Cleaned root canal wall with clinical output #2B from the endodontic application.

FIG. 5F

Case 3A
Before Cleaning

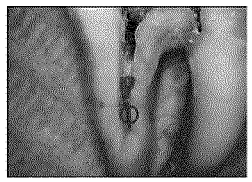

Output# 3B: if the probing
root canal underneath the
tip & debris present.

**Changes in PTR Amp, PTR Phase
LUM Phase Before Cleaning**

PTR Amp: 59.3 +/- 8.2
PTR Phase: 31.6 +/- 13.6
LUM Phase: 173.0 +/- 2.1

Test 1:
A: (PTR-Amp)/(PTR-Amp-std) > Ref A1 (=5) &
B: (PTR-Ph)/(PTR-Ph-std) > Ref P1 (5)
Test 2:
A: (PTR-Amp)/(PTR-Amp-std) > Ref A2 (=2) &
B: (PTR-Ph)/(PTR-Ph-std) > Ref P2 (2)

Test 3:
(LUM-Phase shift) < Ref B (=1 )

Test 1 : Before cleaning: Failed
PTR Amp/PTR-Amp-std = 59.3 / 8.2 = 7.2 < Ref A1(=5) &
PTR Phase/PTR Ph-std = 31.6 / 13.6 = 2.3 < Ref P1 (=5)

Test 2 : Before cleaning: Passed
PTR Amp/PTR-Amp-std = 59.3 / 8.2 = 7.2 > Ref A2(=2) &
PTR Phase/PTR Ph-std = 31.6 / 13.6 = 2.3 > Ref P2 (=2)

Test 3: Before cleaning : Failed.
LUM Phase: 180-173.0=7.0 > Ref B (1.0)

Case 3A: Output #3B:

Early demin/carious dentin
wall. Mild cleaning needed
to remove soft surface
debris and to treat early
dentin demin/carious wall.

Case 3A results were scanned before cleaning the root canal. The wall had early demin and soft
debris on dentin wall as demonstrated with clinical output #3B from the endodontic application.

FIG. 5H

**Changes in PTR Amp, PTR Phase
LUM Phase After Cleaning**

Test 1:
A: (PTR-Amp)/(PTR-Amp-std) > Ref A1 (=5) &
B: (PTR-Ph)/(PTR-Ph-std) > Ref P1 (5)
Test 2:
A: (PTR-Amp)/(PTR-Amp-std) > Ref A2 (=2) &
B: (PTR-Ph)/(PTR-Ph-std) > Ref P2 (2)

Test 3:
(LUM-Phase shift) < Ref B (=1 )

PTR Amp: 13.5 +/- 9.3
PTR Phase: 35.7 +/- 21.1
LUM Phase: 172.8 +/- 3.3

Case 3B  After Cleaning

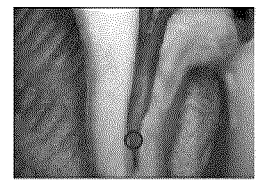

Output #2: If the probing
root canal beneath the tip
is clean of debris.

Test 1 : After cleaning: Failed
PTR Amp/PTR-Amp-std = 13.5 / 9.3 = 1.5 < Ref A1(=5) &
PTR Phase/PTR Ph-std = 35.7 / 21.1 = 1.7 < Ref P1 (=5)

Test 2 : After cleaning: Failed
PTR Amp/PTR-Amp-std = 13.5 / 9.3 = 1.5 < Ref A2(=2) &
PTR Phase/PTR Ph-std = 35.7 / 21.1 = 1.7 < Ref P2 (=2)

Test 3: After cleaning : Failed.
LUM Phase: 180-172.8=7.2 > Ref B (1.0)

Case 3B: Output #2B:

Healthy dentin wall.
Cleaned root canal wall
but with a drop (>1
degree) in backscattered
surface LUM in Phase
from particles on wall.

As seen on the photo of the scan spot, Case 3B results were scanned after cleaning the root
canal, PTR-Amp, PTR Phase in Healthy range. But the surface wall still had micro scale particles
deposited on the wall (due to failed Test 3). Cleaned root canal wall with clinical output #2B
Was obtained from the endodontic application.

FIG. 5I

At this level the scans are detecting caries and also some of the pulp chamber roof

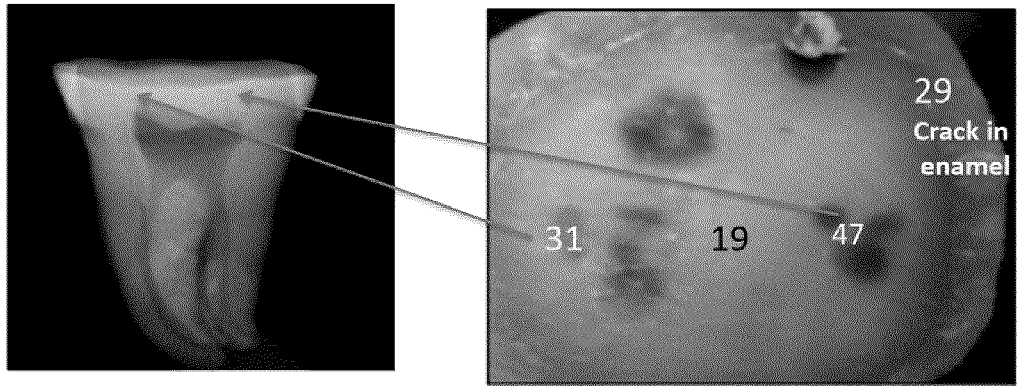

At this level the scans are detecting caries and also some of the pulp chamber roof

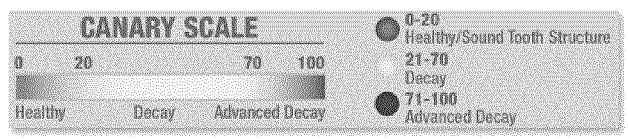

CN ≥ 30 are detecting caries / demineralization.
Scans done in center of each box.

FIG. 6D

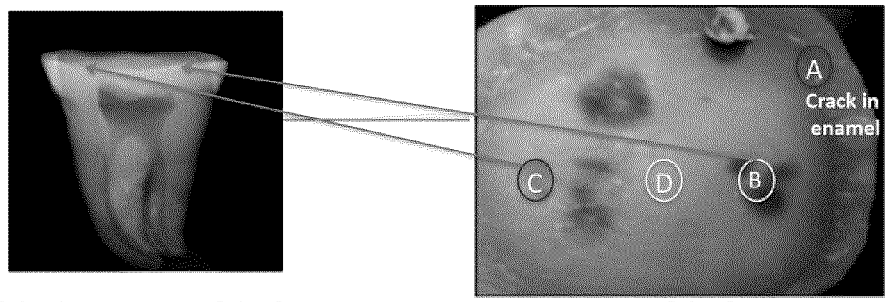

Point: A
PTR Amp/PTR-Amp-std = 19.3 / 2.4 =8.0 (>5)
PTR Phase/PTR Ph-std = 41.9 / 8.5 =5 (>5)
LUM Phase: 180-179.9 =0.1 < Ref B (1.0)
Test 1 passed.
Test 2 passed
Test 3 passed
⬇
Crack
Output 4A Point: B
PTR Amp/PTR-Amp-std = 108.0 / 3.5 =30.9 (>5)
PTR Phase/PTR Ph-std =24.7 / 3.6 =6.8 (>5)
LUM Phase: 180-179.7 =0.3 < Ref B (1.0)
Test 1 passed.
Test 2 passed
Test 3 passed
⬇
Crack
Output 4A Point: C
PTR Amp/PTR-Amp-std = 23.1 / 2.4 =9.6 (>5)
PTR Phase/PTR Ph-std = 39.9 / 3.9 =10.2 (>5)
LUM Phase: 180-179.8 =0.2 < Ref B (1.0)
Test 1 passed
Test 2 passed
Test 3 passed
⬇
Crack
Output 4A Point: D
PTR Amp/PTR-Amp-std = 13.2 / 1.7 =7.8 (>5)
PTR Phase/PTR Ph-std = 32.3 / 15.1 =2.1 (<5)
LUM Phase: 180-179.9 =0.1 < Ref B (1.0)
Test 1 failed
Test 2 passed
Test 3 passed
⬇
Early Demin/Crack
Output 3A

FIG. 6E

Scan now picking up pulp horn.
Cross-section has removed all caries

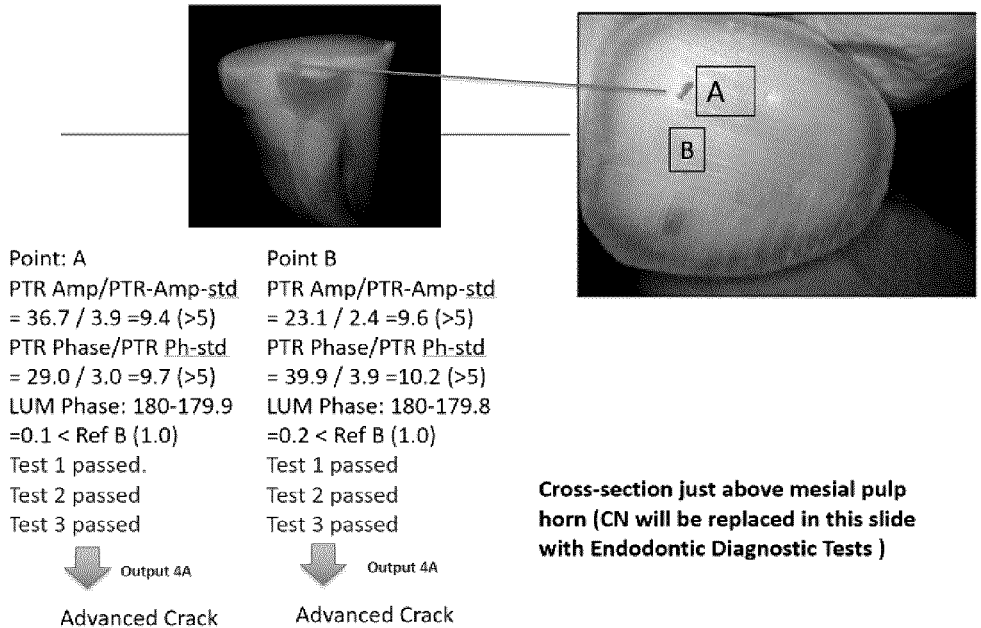

Point: A
PTR Amp/PTR-Amp-std
= 36.7 / 3.9 =9.4 (>5)
PTR Phase/PTR Ph-std
= 29.0 / 3.0 =9.7 (>5)
LUM Phase: 180-179.9
=0.1 < Ref B (1.0)
Test 1 passed.
Test 2 passed
Test 3 passed
⬇ Output 4A
Advanced Crack Point B
PTR Amp/PTR-Amp-std
= 23.1 / 2.4 =9.6 (>5)
PTR Phase/PTR Ph-std
= 39.9 / 3.9 =10.2 (>5)
LUM Phase: 180-179.8
=0.2 < Ref B (1.0)
Test 1 passed
Test 2 passed
Test 3 passed
⬇ Output 4A
Advanced Crack

Cross-section just above mesial pulp horn (CN will be replaced in this slide with Endodontic Diagnostic Tests )

Points: A,B-Advanced cracks due to drilling and ready to reach the pulp chamber.

FIG. 6G

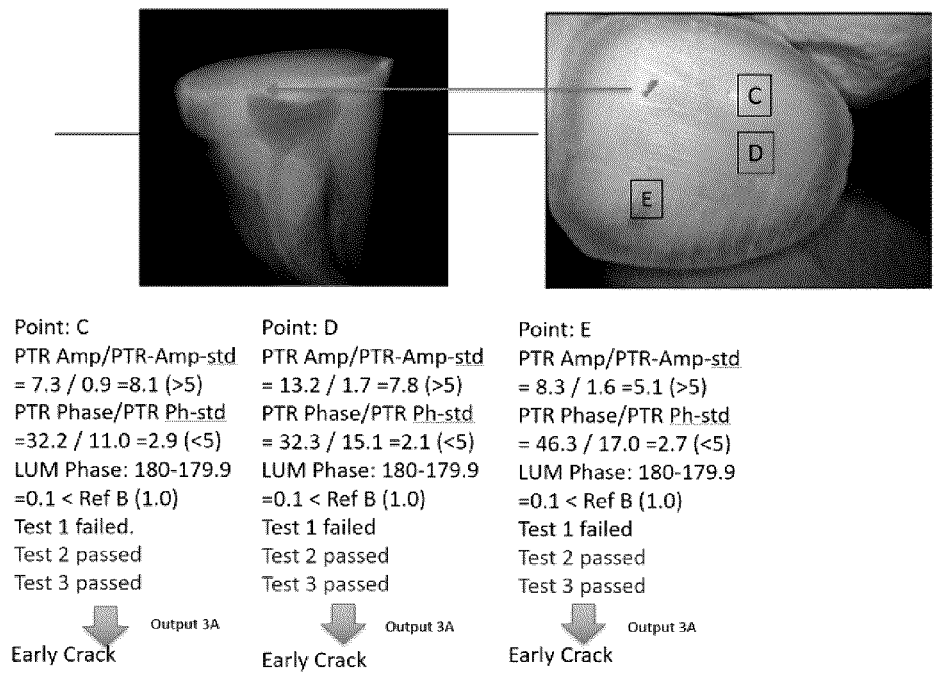

Point: C
PTR Amp/PTR-Amp-std
= 7.3 / 0.9 =8.1 (>5)
PTR Phase/PTR Ph-std
=32.2 / 11.0 =2.9 (<5)
LUM Phase: 180-179.9
=0.1 < Ref B (1.0)
Test 1 failed.
Test 2 passed
Test 3 passed
⬇ Output 3A
Early Crack Point: D
PTR Amp/PTR-Amp-std
= 13.2 / 1.7 =7.8 (>5)
PTR Phase/PTR Ph-std
= 32.3 / 15.1 =2.1 (<5)
LUM Phase: 180-179.9
=0.1 < Ref B (1.0)
Test 1 failed
Test 2 passed
Test 3 passed
⬇ Output 3A
Early Crack Point: E
PTR Amp/PTR-Amp-std
= 8.3 / 1.6 =5.1 (>5)
PTR Phase/PTR Ph-std
= 46.3 / 17.0 =2.7 (<5)
LUM Phase: 180-179.9
=0.1 < Ref B (1.0)
Test 1 failed
Test 2 passed
Test 3 passed
⬇ Output 3A
Early Crack Point C,D E- Early cracks and more drilling needed at this area to reach to the pulp chamber

FIG. 6H

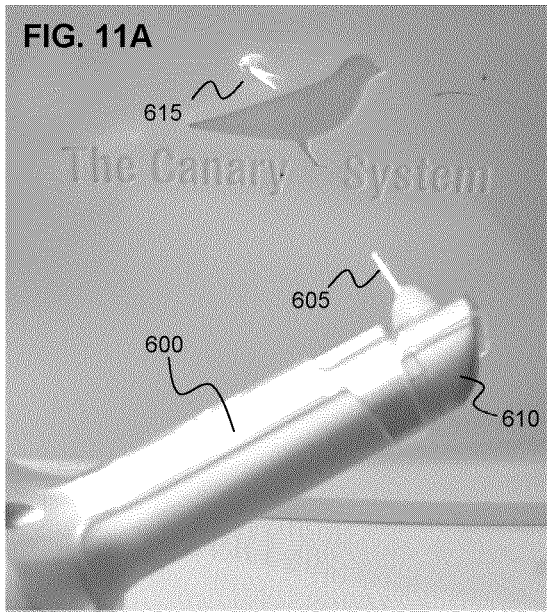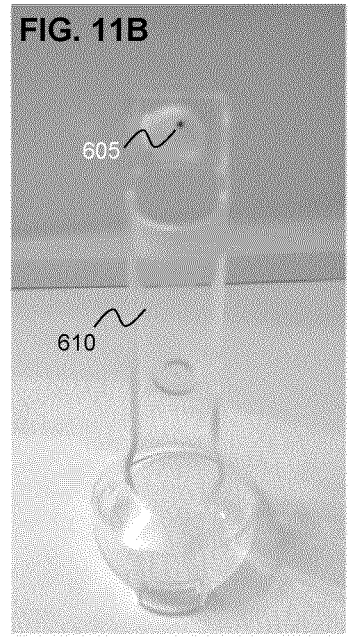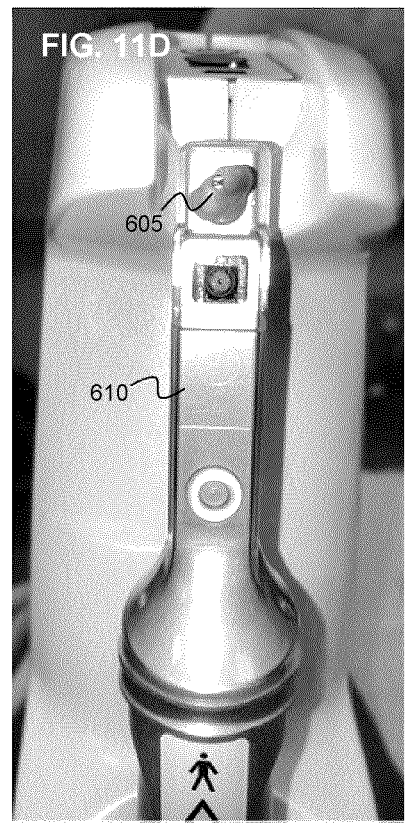

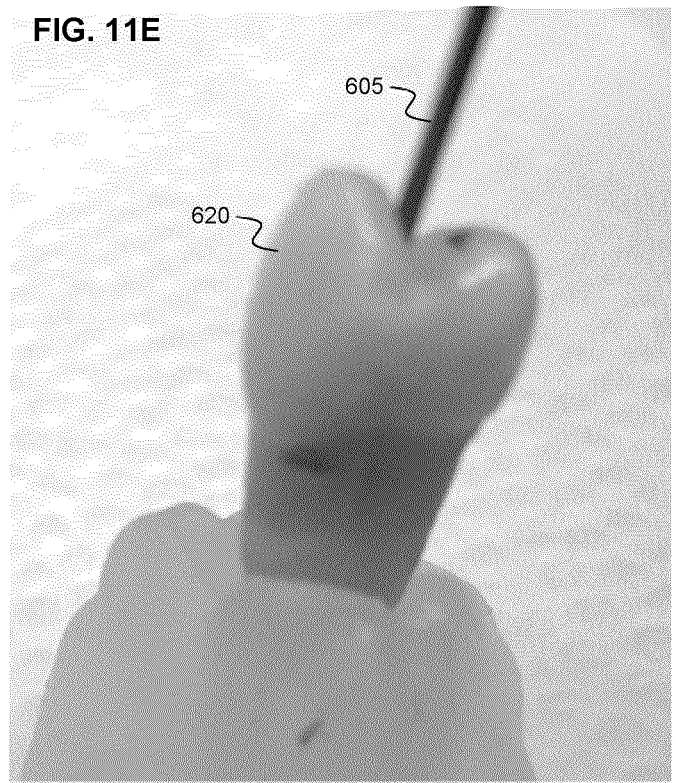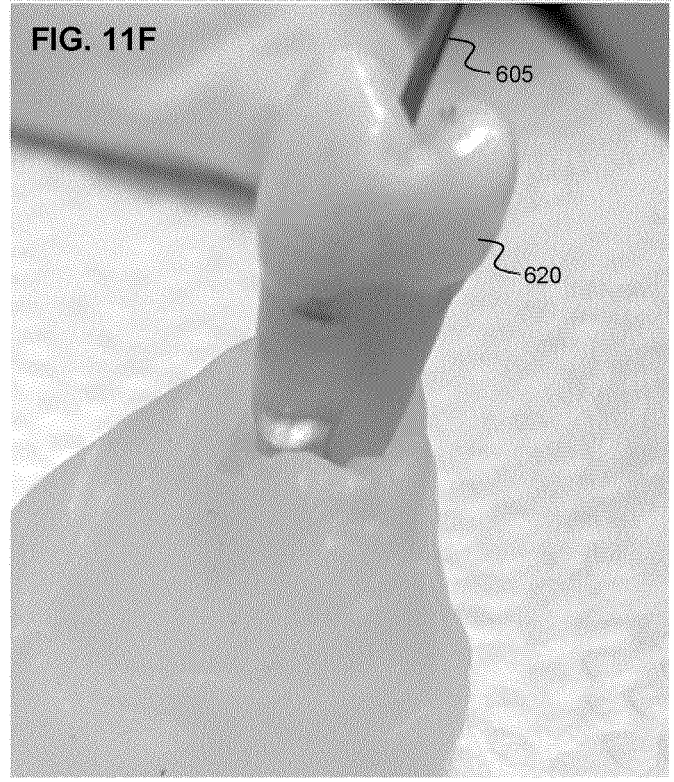

DEVICES AND METHODS FOR THE INTRA-OPERATIVE VERIFICATION OF ORAL HEALTH PROCEDURES

CROSS-REFERENCE TO RELATED APPLICATION

This application is a National Phase application claiming the benefit of the international PCT Patent Application No. PCT/CA2019/051868, filed on Dec. 19 2019, in English, which claims priority to U.S. Provisional Application No. 62/784,173, titled "DEVICES AND METHODS FOR THE INTRA-OPERATIVE VERIFICATION OF ORAL HEALTH PROCEDURES" and filed on Dec. 21, 2018, the entire contents of which are incorporated herein by reference.

BACKGROUND

The present disclosure relates to oral health diagnostics. In particular, the present disclosure relates to endodontic (root canal) procedures.

Endodontic treatment or root canal therapy involves the cleansing, shaping and obturating (filling) the root canal system of a tooth. The objective of a root canal procedure is to clean out the soft tissue debris (pulp or nerve tissue) from the root canal system and then obturate or fill the space to prevent bacterial re-invasion. The root canal system is made accessible after first having accessed the pulp chamber through drilling a hole in the tooth. The various root canals open into the base of the pulp chamber. After accessing the root canal system, it is cleaned via mechanical instrumentation with rotary files or hand instruments or using sonic irrigation systems or possibly low powered lasers. A cleaning procedure also typically involves irrigation using ultrasonics or sonic systems or irrigating with a syringe using a variety of fluids. Fluids are designed to remove soft tissue debris, soften any calcified areas and open up any small orifices, lateral canals or canal entrances.

Unfortunately, conventional endodontic treatment techniques have a number of associated limitations. In particular, the inability to clean and shape root canals, especially those canals which are not cylindrical, very small or have a high degree of curvature, which can lead to repeated infections and post-operative pain. Conventional endodontic methods also render clinicians unable to locate smaller accessory canals, such as, for example, MB2 canals in maxillary molars. Another disadvantage associated with conventional practices is that they prevent the clinician from being able to open and clean small lateral canals that run along the walls of the root canal system.

Conventional endodontic treatment modalities can also present undue risk to the patient. For example, the unnecessary removal of hard tissue (dentin) from the interior of the root canal system during conventional endodontic treatment weakens the tooth. Moreover, the fracture of instruments within the root canal is known to occasionally occur with conventional methods, with a fracture incidence of approximately 3%. Furthermore, conventional methods also present a danger of perforating the root system if burs are employed to open root canal entrances or orifices or to clean the walls of the root canal system.

SUMMARY

An intraoral optical probe is provided that includes a distal elongate optical waveguide for interrogating dental tissue. In some example embodiments, the elongate optical waveguide has dimensions suitable for the insertion of the waveguide into an exposed root canal. According to various example embodiments, the elongate optical waveguide, when inserted into an internal region of a tooth, can direct incident optical radiation from the intraoral optical probe directly onto an inner surface, such as an internal surface of a root canal, such that status of the root canal can be interrogated directly. The intraoral optical probe may be employed to provide intraoperative feedback regarding internal dental tissue, such as interoperative feedback pertaining to the interior of the root canal during an endodontic procedure.

Accordingly, in a first aspect, there is provided an intraoral optical system for performing assessment of an endodontic procedure, the intraoral optical system comprising:
  a body suitable for use in a handheld configuration;
  a modulated light source housed within the body;
  an elongate optical waveguide extending from a distal region of the body, and wherein said elongate optical waveguide is in optical communication with said modulated light source for delivering incident modulated optical energy to dental tissue when said elongate optical waveguide is inserted into an interior region of a tooth and for collecting luminescence energy responsively emitted from the dental tissue;
  an optical detector capable of detecting the luminescence energy collected by said elongate optical waveguide; and
  processing circuitry operatively coupled to said modulated light source and said optical detector, wherein said processing circuitry comprises memory coupled with one or more processors to store instructions, which when executed by said one or more processors, causes said one or more processors to perform operations comprising:
    processing luminescence signals obtained from said optical detector to determine a luminescence phase associated with detected luminescence energy relative to a reference phase associated with said modulated light source; and
    employing the luminescence phase to detect a presence of debris on an internal surface associated with the dental tissue.

In another aspect, there is provided an intraoral optical system comprising:
  a body suitable for use in a handheld configuration;
  a modulated light source housed within the body;
  one or more distal focusing and collection optical components located remote from a proximal region of the body, wherein the one or more distal focusing and collection optical components is in optical communication with the modulated light source for delivering incident modulated optical energy to dental tissue and for collecting luminescence energy responsively emitted from the dental tissue;
  a detector capable of detecting collected luminescence energy; and
  processing circuitry operatively coupled to the modulated light source and the detector, wherein said processing circuitry comprises memory coupled with one or more processors to store instructions, which when executed by said one or more processors, causes said one or more processors to perform operations comprising:
    processing luminescence signals obtained from the detector to determine a luminescence phase associated with detected luminescence energy relative to a reference phase associated with the modulated light source; and employing the luminescence phase to determine a status of the dental tissue, such that the status is determined, at least in part, based on a comparison between the luminescence phase and a pre-determined phase value.

In another aspect, there is provided an intraoral optical system comprising:
a body suitable for use in a handheld configuration;
a modulated light source housed within the body;
one or more distal focusing and collection optical components located remote from a proximal region of the body, wherein the one or more distal focusing and collection optical components is in optical communication with the modulated light source for delivering incident modulated optical energy to dental tissue and for collecting luminescence energy responsively emitted from the dental tissue;
an optical detector capable of detecting the luminescence energy; and
processing circuitry operatively coupled to said modulated light source and said optical detector, wherein said processing circuitry comprises memory coupled with one or more processors to store instructions, which when executed by said one or more processors, causes said one or more processors to perform operations comprising:
processing luminescence signals obtained from said optical detector to determine a luminescence phase associated with detected luminescence energy relative to a reference phase associated with said modulated light source; and
employing the luminescence phase to detect a presence of debris on an internal surface associated with the dental tissue.

In another aspect, there is provided a method of performing assessment of an endodontic procedure using an intraoral probe;
the intraoral probe comprising:
a body suitable for use in a handheld configuration;
a modulated light source housed within the body, wherein the modulated light source is configured to generate incident modulated optical energy;
an elongate optical waveguide extending from a distal region of the body, wherein the elongate optical waveguide is in optical communication with the modulated light source; and
an optical detector;
the method comprising:
after inserting the elongate optical waveguide into an interior region of a tooth, employing the intraoral probe to deliver the incident modulated optical energy to dental tissue;
collecting luminescence energy responsively emitted from the dental tissue and detecting luminescence signals with the optical detector;
processing the luminescence signals to determine a luminescence phase associated with detected luminescence energy relative to a reference phase associated with the modulated light source; and
employing the luminescence phase to detect a presence of debris on an internal surface associated with the dental tissue.

In another aspect, there is provided a method identifying a location of a pulp chamber during an endodontic procedure using an intraoral probe, the intraoral probe comprising:
a body suitable for use in a handheld configuration;
a modulated light source housed within the body, wherein the modulated light source is configured to generate incident modulated optical energy;
an elongate optical waveguide extending from a distal region of the body, wherein the elongate optical waveguide is in optical communication with the modulated light source;
a first optical detector configured to detect luminescence energy; and
a second optical detector configured to detect photothermal energy;
the method comprising:
after inserting the elongate optical waveguide into an access hole within the surface of a tooth, employing the intraoral probe to deliver the incident modulated optical energy to dental tissue within the access hole;
collecting the luminescence energy responsively emitted from the dental tissue and detecting luminescence signals with the first optical detector;
collecting the photothermal energy responsively emitted from the dental tissue and detecting photothermal signals with the second optical detector; and
processing the luminescence signals and the photothermal signals to identify a presence of the pulp chamber below the access hole.

In another aspect, there is provided a method of detecting a root canal apex or opening of the root canal system into the surrounding alveolar bone during an endodontic procedure using an intraoral probe, the intraoral probe comprising:
a body suitable for use in a handheld configuration;
a modulated light source housed within the body, wherein the modulated light source is configured to generate incident modulated optical energy;
an elongate optical waveguide extending from a distal region of the body, wherein the elongate optical waveguide is in optical communication with the modulated light source;
a first optical detector configured to detect luminescence energy; and
a second optical detector configured to detect photothermal energy;
the method comprising:
after inserting the elongate optical waveguide into a root canal, employing the intraoral probe to deliver the incident modulated optical energy within the root canal;
collecting the luminescence energy responsively emitted from the dental tissue and detecting luminescence signals with the first optical detector;
collecting the photothermal energy responsively emitted from the dental tissue and detecting photothermal signals with the second optical detector; and
processing the luminescence signals and the photothermal signals to determine when a distal region of the elongate optical waveguide is positioned proximal to the apex of the root canal.

In another aspect, there is provided a method of detecting a location of an unexposed root canal from the floor of a pulp chamber during an endodontic procedure using an intraoral probe, the intraoral probe comprising:
a body suitable for use in a handheld configuration;
a modulated light source housed within the body, wherein the modulated light source is configured to generate incident modulated optical energy;
an elongate optical waveguide extending from a distal region of the body, wherein the elongate optical waveguide is in optical communication with the modulated light source;
a first optical detector configured to detect luminescence energy; and
a second optical detector configured to detect photothermal energy;

the method comprising:
    after inserting the elongate optical waveguide into the pulp chamber, employing the intraoral probe to deliver the incident modulated optical energy onto a floor of the pulp chamber, performing luminescence and photothermal measurements at a plurality of locations by:
        collecting the luminescence energy responsively emitted from the dental tissue and detecting luminescence signals with the first optical detector;
        collecting the photothermal energy responsively emitted from the dental tissue and detecting photothermal signals with the second optical detector; and
        processing the luminescence signals and the photothermal signals to determine one or more measures; and
    identifying a location of an unexposed root canal by comparing the one or more measures to respective reference values.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1B and 1C show an example of photothermal measurements made according to a grid that divides the tooth surface into a set of different spatial regions.

FIGS. 4A-4J illustrate example methods of employing an intraoral optical probe for verifying different stages of an endodontic procedure.

FIGS. 5A-5L illustrate an example method of performing intraoperative verification of an endodontic procedure.

FIGS. 6A-6H illustrate an example method of detecting the presence of a pulp chamber during an endodontic procedure.

FIGS. 11A-11F are photographs of an example intraoral optical probe and the ex-vivo optical interrogation of the root canal of a tooth via insertion of the elongate optical waveguide.

DETAILED DESCRIPTION

Figure 1A:
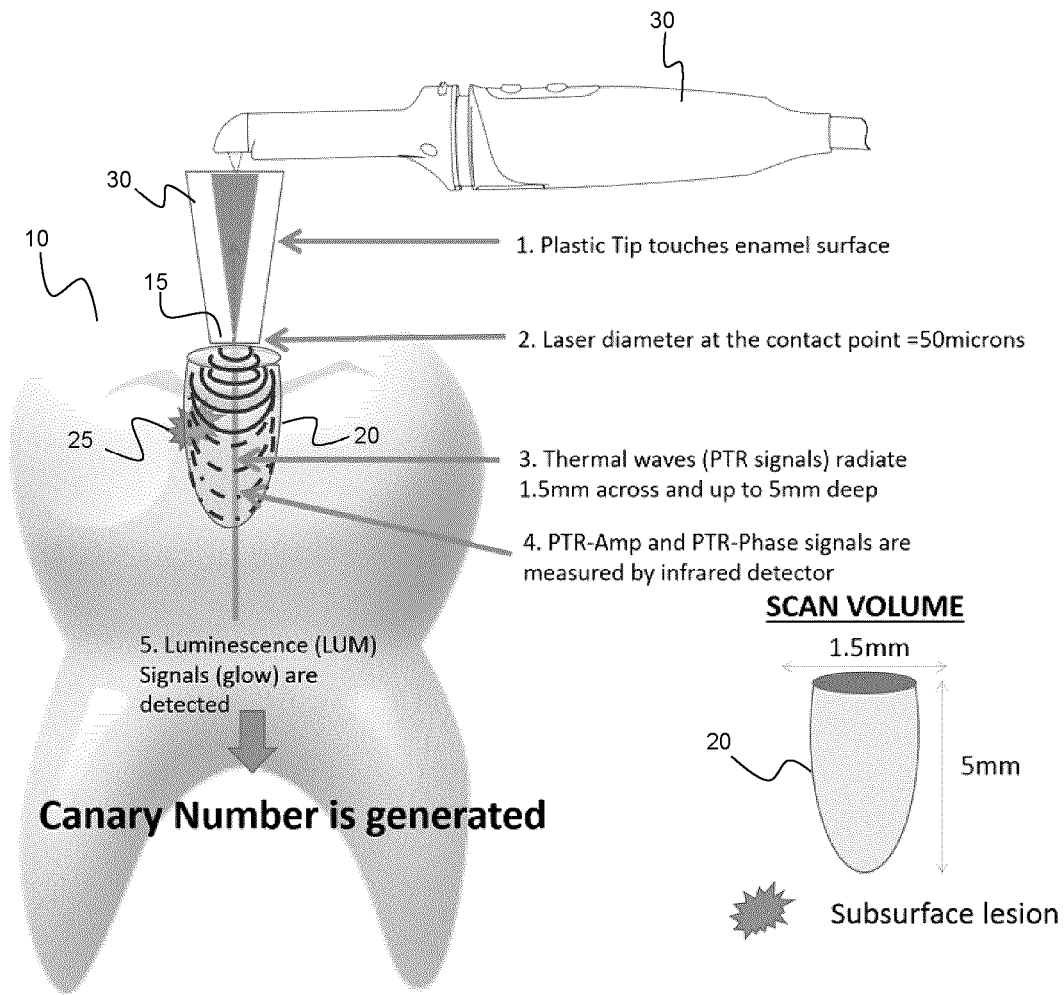
FIG. 1A illustrates a conventional method of performing photothermal measurements on an external tooth surface using an intraoral optical probe.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As described above, conventional methods of performing endodontic procedures can lead to an array of technical problems that can present hazards for the patient. In considering the nature of these problems, the present inventors recognized that their origin arises from a lack of an ability to sufficiently examine the walls of the root canal. Moreover, the present inventors found that conventional imaging methods do not provide sufficient resolution or specificity to reveal insufficient cleaning of a given root canal or cracks or tooth decay on the walls of the root canal, and can also fail to provide a suitable determination of the cleanliness of additional root canals that may be present and/or fail to determine the location of the apex of a particular root canal. This lack of intraoperative knowledge regarding the cleanliness and structure of the root canal leads to potentially negative outcomes for patients.

According to example embodiments of the present disclosure, various example devices and methods are provided in which a handheld intraoral optical probe may be employed to provide intraoperative feedback regarding internal dental tissue including information on dentin, cementum and pulp tissue, and integrity of the root canal wall, during a dental procedure, such as interoperative feedback pertaining to the interior of the root canal during an endodontic procedure.

The example embodiments disclosed herein represent a significant and unconventional departure from optical diagnostic devices known in the art and their associated methods of use. In particular, conventional intraoral devices, such as the Canary System® Diagnodent System, and SPECTRA System are conventionally employed for caries detection of external surfaces of teeth. For example, FIG. 1A illustrates an example diagnostic modality know in the art in which modulated photothermal and luminescence detection is employed for the detection of subsurface defects in teeth via the direction of an incident optical beam onto an external surface of a tooth. As shown in the figure, an intraoral optical probe 30 is employed to generate a beam of incident optical energy that is directed onto the surface of tooth 10, forming spot 15. The absorbed optical energy responsively produces photothermal waves and generates luminescence, which probe a region 20 including both the surface region and the subsurface region. As shown in the figure, a subsurface lesion 25 generates a perturbation to the photothermal and luminescence signals that are detected by the probe. Examples of photothermal/luminescence-based probe systems are described in Patent Cooperation Treaty Application No. PCT/CA2011/50303, titled "HANDPIECE WITH INTEGRATED OPTICAL SYSTEM FOR PHOTOTHERMAL RADIOMETRY AND LUMINESCENCE MEASUREMENTS", and filed on May 13, 2011, which is incorporated herein by reference in its entirety.

As shown in FIG. 1A, the intraoral optical probe 30 directs the incident beam onto a small spot on the tooth surface. Although the figure shows a plastic tip 30 employed in conjunction with the intraoral optical probe, this tip is merely provided to shroud the optical beam without interacting with the optical beam. In other words, the plastic tip 30 functions merely as device the facilitates the correct placement of the intraoral optical probe relative to the tooth being examined, and the plastic tip 30 does not function as an optical waveguide. Furthermore, the tip 30 fails to provide high positional accuracy on the external surface of the tooth.

During clinical practice, it may be important or beneficial to scan a specific location on the tooth surface. For example, as shown in FIGS. 1B and 1C, measurements may be made according to a grid that divides the tooth surface into a set of different spatial regions. The diagnostic measurements from the regions may then be obtained and displayed on an image of the tooth surface, as shown in the figures. Unfortunately, such an approach fails to provide diagnostic information pertaining to internal tooth structures, such as a root canal (e.g. pertaining to walls of the root canal or the location of the apex of the root canal), as the external nature of the beam requires that the beam penetrates though large regions of enamel and dentin before reaching the pulp chamber and interacting with the root canal or the interior walls of the root canal. Examining the root system from the exterior involves having the beam penetrate gum tissue, bone, cementum and then dentin before reaching the interior of the root canal.

These problems may be overcome by various embodiments of the present disclosure in which an intraoral optical probe is provided that is configured having a distal elongate optical waveguide. In some example embodiments, the elongate optical waveguide has dimensions suitable for the insertion of the waveguide into an exposed root canal. According to such example embodiments, the elongate optical waveguide, when inserted into the root canal, can direct incident optical radiation from the intraoral optical probe directly onto an inner surface of the root canal or the interior of the root canal, such that status of the root canal can be interrogated directly and internally and without loss of signal and specificity that would otherwise occur when performing external measurements through an external surface of the tooth.

Figure 2A:
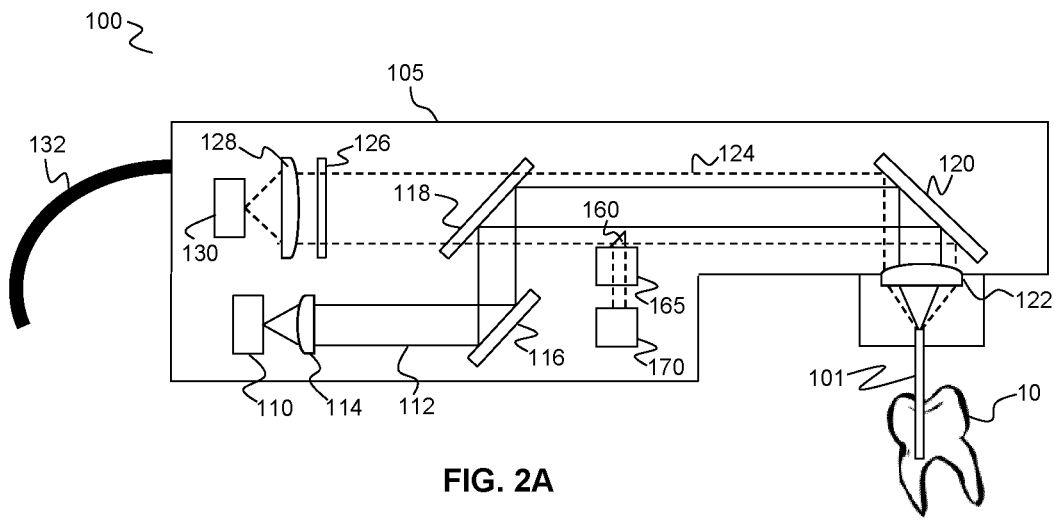
FIG. 2A is a schematic illustration of an example handheld intraoral optical probe for measuring internal regions of a tooth.

FIG. 2A illustrates an example embodiment of an intraoral optical probe 100 that is suitable for performing direct internal measurements of a root canal system using an elongate optical waveguide. The example intraoral optical probe 100 includes a handheld body (housing) 105, which houses a diagnostic detection subsystem and supports the elongate optical waveguide 101. The diagnostic detection subsystem, in the present example and non-limiting embodiment, includes an optical source 110 which generates incident optical beam 112 (an incident optical energy beam) that is collimated by lens 114, is reflected off a mirror 116 and a dichroic mirror 118, before being deflected by a mirror 120 and focused into the elongate optical waveguide 101 by a lens 122.

The elongate optical waveguide 101 is shown with its distal region inserted an exposed root canal. The incident optical energy is directly delivered by the elongate optical waveguide 101 into the root canal. The incident optical energy is directed onto an inner surface of the root canal, and responsively generates optical signals, such as luminescence, fluorescence, and/or photothermal radiation, at the root canal surface and/or beneath the root canal surface.

These optical signals are collected by the distal end of the elongate optical waveguide 101 and collimated by the lens 122 to form the collected optical beam 124, which is directed within the body 105 by the mirror 120. The first dichroic mirror 118 rejects the incident optical energy that is scattered back into the handheld probe, and selectively transmits the optical signals generated at or within the root canal surface. These transmitted signals are then optionally spectrally filtered by optical filter 126 (e.g. a high-pass filter) and focused by a lens 128 onto a detector 130. In the example embodiment shown in FIG. 2A, control signals (for controlling the optical source 110) and received signals from the detector 130 are transmitted through cable 132 to a control and processing unit (described further below). Alternatively, the control signals and/or detected signals may be transmitted wirelessly. In another example implementations, processing electronics may be included within the body 105 for partial or complete processing of control signals and/or received signals.

The example embodiment shown in FIG. 2A may be implemented according to a number of different optical modalities, including, but not limited to, luminescence detection, fluorescence detection, and photothermal detection. In one example implementation, the optical source 110 may be selected to generate fluorescence signals in dental tissue, and the detector 130 may be a visible or infrared detector suitable for detecting fluorescence signals.

For example, in one implementation, the optical components of the diagnostic detection system may be configured for photothermal and luminescence detection as per the example embodiments described and illustrated in Patent Cooperation Treaty Application No. PCT/CA2011/50303. For example, the light source 110 may be a modulated light source (modulated by driver electronics/circuitry) for generating photothermal waves and luminescence in dental tissue, such as a modulated laser diode having a wavelength of approximately 660 nm, which is capable of simultaneously generating luminescence and photothermal signals in dental tissue, and the detector 130 may be an infrared detector, such as a photovoltaic HgCdZnTe detector (which may optionally be cooled via an integrated thermo-electric cooler) or an InAsSb detector. Lock-in detection may be employed to provide a sufficient signal-to-noise ratio, for example, using a software-based lock-in detector configured to perform lock-in detection according to a reference waveform that is employed to modulate the optical source 110.

An additional infrared detector and associated optical filter may also be included for the detection of luminescence signals. For example, as shown in FIG. 2A, a portion of the collected luminescence beam may encounter a beam sampling element, such as pickoff prism 160 (or another suitable element, such as a filter) and is directed towards the optical filter 165 and the photodetector 170. The optical filter 165 removes unwanted reflected and scattered laser light, and the photodetector 170 is selected to have a spectral response suitable for the detection of the collected luminescence. In one example, the photodetector 170 may be a silicon photodiode, and the optical filter 165 may be an inexpensive color glass filter having a bandwidth and optical density matched to the laser wavelength and power (such as RG 715 longpass color filter).

In such an example embodiment, a diagnostic measure may be generated by combining photothermal and luminescence signals into a single measure. For example, the Canary System® generates a "Raw Canary Number" based on the combination of photothermal and luminescence signals according to the following formula:

$$CanaryNumber(raw) = rCN = C \left| \frac{PTR_{Amp} \cdot PTR_{Phase}}{LUM_{Amp} \cdot LUM_{Phase}} \right|$$

where $PTR_{Amp}$=photothermal amplitude, $PTR_{Phase}$=photothermal phase, $LUM_{Amp}$=luminescence amplitude, $LUM_{Phase}$=luminescence phase, and C is an instrumental normalization constant. In some example implementations, this measure, referred to above as the "Raw Canary Number", can be converted into a logarithmic measure, which is henceforth referred to as the "Canary Number" as follows:

$$C\,N(i) = a(i)\ln(C(i)) + b(i)$$

where i=1, 2, 3 denote three zones, such that:
  i=1 [Healthy Zone (0-20)];
  i=2 [Early Caries Zone (21-70)];
  i=3 [Advanced Caries Zone (71-100)];
    C(i)=Raw Canary Number (shown above), an input value;
    a(i)=slope of the line in Zone (i); and
    b(i)=y-intercept of the line in Zone (i).
The variables 'a(i)' and 'b(i)' are unique to each zone and are determined using the following equations:

$$a(i) = \frac{[CN(i)_{max} - CN(i)_{min}]}{\left[\ln\left(\frac{C(i)_{max}}{C(i)_{min}}\right)\right]}$$

and $$b(i) = CN(i)_{min} - a(i)\ln[C(i)_{min}],$$

and where $CN(i)_{min}$, $CN(i)_{max}$ are set values and values for $C(i)_{min}$ and $C(i)_{max}$ for zones i=1, 2, 3 are determined for this application from clinical measurements on healthy and carious dentin.

In another example implementation, the optical components of the diagnostic detection system may be configured for themophotonic dynamic imaging, as per the example embodiments described and illustrated in Patent Cooperation Treaty Application No. PCT/CA2012/050035, titled "SYSTEMS AND METHODS FOR THERMOPHOTONIC DYNAMIC IMAGING", and filed on Jan. 20, 2012, which is incorporated herein by reference in its entirety. It will be understood that while the example intraoral optical probe shown in FIG. 2A includes a dual photothermal detection modality, other example implementations of the intraoral optical probe may include one or more optical detection modalities.

Figure 2B:
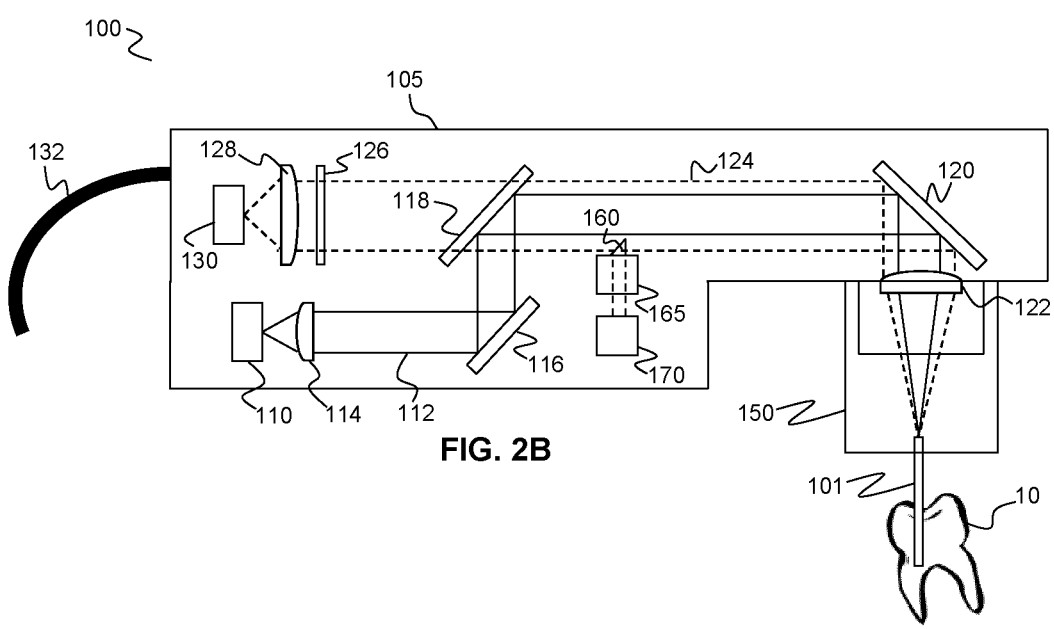
FIG. 2B is a schematic illustration of an alternative example handheld intraoral optical probe in which the elongate optical waveguide is secured to the probe body by a detachable support.

In another example implementation, an existing intraoral optical probe may be retrofitted to include the elongate waveguide. For example, as shown in FIG. 2B, a distal support 150 (e.g. a distal support member, distal adapter, or distal interfacing cap) may support the elongate optical waveguide 101 such that upon attachment of the distal support 150 to the distal region of the intraoral optical probe, the incident light is focused into the elongate optical waveguide 101 (and the collected optical energy is directed into the optical subsystem of the intraoral optical probe). Although not shown in FIG. 2B, the distal support may include one or more additional lenses (or other optical focusing elements) in order to assist with the focusing or collimating the incident optical beam into the elongate optical waveguide, and/or to modify the numerical aperture of the focused incident optical energy that is incident on the elongate optical waveguide.

The distal support 150 may be removably secured to the intraoral optical probe, enabling the clinician to employ the intraoral optical probe for external scanning of a tooth surface, or for internal scanning within a tooth, such as within a root canal, within a pulp chamber or a cavity preparation. The distal support 150 and the intraoral optical probe may include features that enable the repeatable accurate securing of the distal support, such that the incident optical beam is aligned with the entrance aperture of the elongate optical waveguide, such as threaded portions and/or structures that meet in a keyed configuration. The distal support 150 may optionally be provided as a disposable component for use with the intraoral optical probe.

It will be understood that the example embodiments shown in FIGS. 2A and 2B are merely provided as illustrative examples and are not intended to limit the scope of the present disclosure to systems and methods for performing optical diagnostic measurements on teeth. The specific application of the detection of photothermal signals from teeth is provided as a non-limiting example, and other probe configurations, optical modalities, and applications, may be employed without departing from the intended scope of the present disclosure.

The elongate optical waveguide may be any suitable optical waveguide that facilitates the optical guidance of both the incident optical energy and the collected optical signals. The geometry, size and/or composition of the elongate waveguide may vary according to the type of incident optical energy and/or optical signals that collected. For example, the optical waveguide may be a multimode optical fiber. In the case of fluorescence or luminescence detection, the optical fiber may be plastic in order to provide bend resilience and a small bend radius, facilitating use of the elongate optical waveguide within curved (e.g. tortuous) channels within the root canal.

In example embodiments involving the detection of photothermal radiation, the optical waveguide is configured to be transmissive for mid-infrared optical radiation. In one example implementation, a hollow optical fiber may be employed for the elongate optical waveguide.

Figure 3:
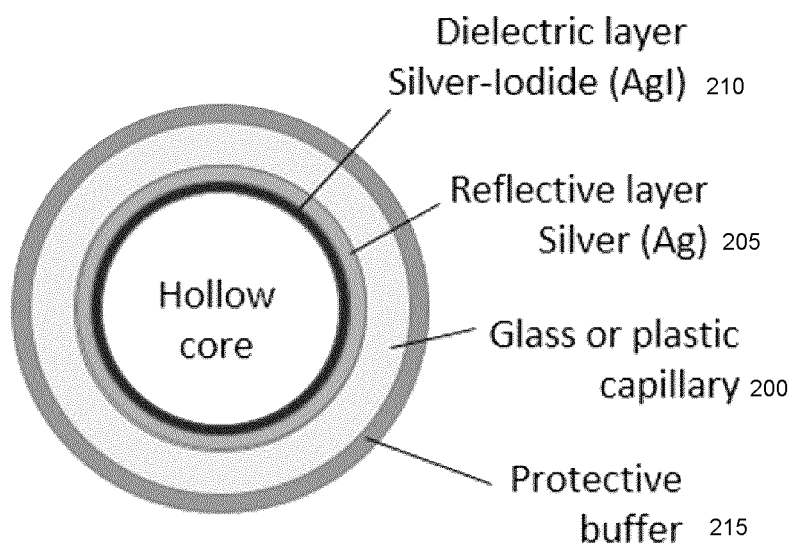
FIG. 3 shows a cross-sectional view of an example hollow optical waveguide.

An example of such a hollow optical fiber is shown in cross-sectional view FIG. 3. The example hollow optical fiber includes a plastic or glass capillary 200 having a reflective layer 205 (e.g. silver) on the inner surface thereof. The inner surface of the reflective layer 205 may be coated with a dielectric layer 210, such as a layer of AgI. A protective outer coating 215 (buffer) may be provided on the outer surface of the capillary 200.

For example, the present inventors have found that a single hollow waveguide may be employed for the collection of photothermal and luminescence energy. In order to perform the experiments disclosed herein, the present inventors employed a plastic hollow waveguide having a length of 2 cm. The specifications of the hollow waveguide were as follows: internal diameter=1500 µm, typical Loss=0.1 dB/m, Output divergence ½ Angle=30 mRad, minimum bend radius=3 cm, maximum power=10 W. As noted above, the internal diameter can be reduced, such as reduced to 250 µm, to achieve additional flexibility. In some example implementations, the inner diameter of the hollow optical fiber may be in the range of 250-1500 µm.

The hollow optical fiber may be sealed at one or both ends thereof. For example, a sealing material may consist of a clear composite resin such as a clear dental sealant that is not filled.

In some example embodiments, it is beneficial for the outer diameter of the elongate optical fiber to have a narrow diameter that facilitates insertion of at least a distal region thereof into a root canal. For example, the outer diameter of the elongate optical waveguide may be less than 0.5-3 mm, facilitating access to the main portion of a typical adult root canal. In some example implementations, the outer diameter of the elongate optical fiber may be less than 0.5-1 mm, facilitating access to the smaller lateral canals and or to areas at the apex which have very narrow diameter a typical root canal.

It is also beneficial for the elongate optical waveguide to provide sufficient flexibility to permit insertion thereof into curved or angled portions of the root system, such as curved portions involving a bend angle of 30-40 degrees. For example, in one example implementation, the maximum bend radius of the elongate optical waveguide is less than 50 mm. In another example implementation, the maximum bend radius of the elongate optical waveguide is less than 20 mm. In another example implementation, the maximum bend radius of the elongate optical waveguide is less than 10 mm. In yet another example implementation, the maximum bend radius of the elongate optical waveguide is less than 3 cm for a 1.5 mm internal diameter plastic hollow waveguide.

In some example embodiments, the elongate optical waveguide may be a disposable component that is discarded after each use. In other example embodiments, the elongate optical waveguide may be sterilized after use. For example, sterilization may be achieved by applying a suitable chemical sterilization media to the tip or having it immersed in the media for a set period of time or exposure to heat under pressure for a set period of time or via steam sterilization.

It will be understood that one or more properties of the optical detection subsystem of the intraoral optical probe may be configured or selected in order to achieve a desired depth sensitivity of the optical signals that are generated when the incident optical energy is delivered to an inner surface of the root canal via the elongate optical waveguide. For example, the wavelength of the incident optical energy may be selected to control the absorption depth. Example wavelengths for achieving suitable depth penetration include 808 mm and 660 nm. In example embodiments involving the generation and detection of photothermal waves, the modulation frequency that is employed to modulate to optical source may be selected in order to control the depth sensitivity of the detected photothermal signals. For example, although the Canary System® typically operates at a modulation frequency of approximately 2 Hz in order to achieve depth sensitivity of several millimeters, the modulation frequency of the optical source for intra-root-canal detection may be selected to be larger in order to reduce the depth sensitivity of the detected photothermal signal, such the detected photothermal signals are predominantly associated with the tissue that is adjacent to or proximal to the root canal inner surface. For example, in one example implementation, the modulation frequency may exceed 10 Hz, while in another example implementation, the modulation frequency may exceed 20 Hz.

Intraoperative Verification of Endodontic Procedures

An intraoral optical probe as described above may be employed according to a wide variety of clinical procedures involving the preoperative, intraoperative, and postoperative detection of tissue within internal regions of a tooth. For example, an intraoral optical probe having a distal elongate optical waveguide suitable for insertion within a root canal may be employed for intraoperative verification of one or more stages of an endodontic procedure.

In one example implementation, once the entrance of each of the root canals had been located and entered with a small hand file, drill bit or other instrument, the elongate optical waveguide of the intraoral optical probe may be inserted into the interior of the root canal to examine and measure the interior of the root canal system.

Figures 4A, 4B, 4C:
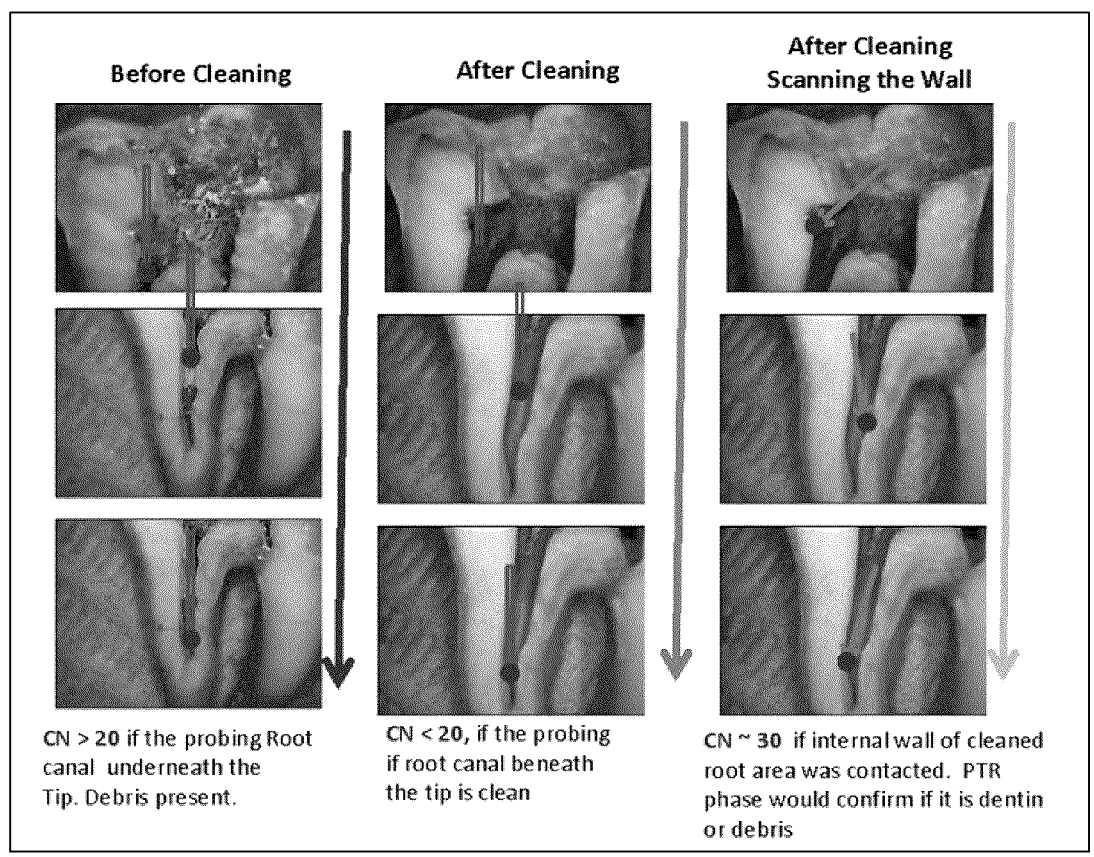

For example, in one example embodiment, an intraoral optical probe may be employed for endodontic procedure verification by determining whether or not debris resides inside the root canal system before and/or after a cleaning procedure is performed on the root canal system. Referring now to FIGS. 4A-4C, an example method is illustrated in which photothermal and luminescence measurements made with an intraoral optical probe having a distal elongate optical waveguide are employed to interrogate the status of a root canal during a root canal procedure. FIG. 4A illustrates the detection of the presence of debris on the inner surface of the root canal prior to cleaning based on the example criteria of a Canary Number reading of greater than 20. After a cleaning operation, as shown in FIG. 4B, a Canary Number of less than 20 is indicative of a successful cleaning operation. As shown in FIG. 4C, after cleaning the root canal, if the Canary Number is greater than 20 (e.g. approximately 30 as shown in the figure), the phase of the photothermal signal may be employed to determine whether or not the distal end of the elongate optical waveguide is contacting dentin or debris.

Figure 4D:
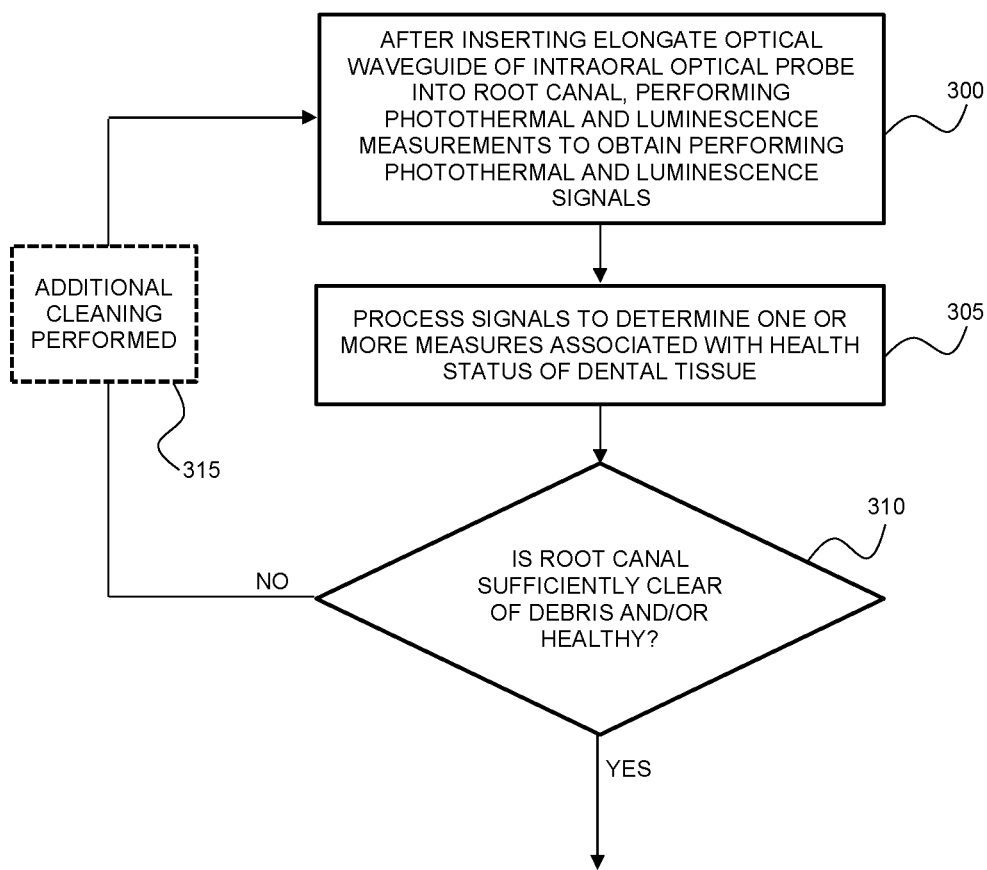

FIG. 4D illustrates an example method in which an intraoral optical probe capable of photothermal and luminescence detection is employed for the intraoperative verification of an endodontic procedure. As shown at step 300, after inserting (introducing) the elongate optical waveguide of the intraoral optical probe into a root canal, photothermal and luminescence measurements are performed by employing the intraoral probe to deliver incident modulated optical energy to dental tissue associated with an inner surface of the root canal, collecting photothermal and luminescence energy responsively emitted from the dental tissue, and detecting photothermal and luminescence signals with optical detectors respectively capable of detecting photothermal and luminescence signals. In step 305, the photothermal and luminescence signals are processed to determine one or more health status measures associated with the dental tissue. For example, the Canary Number may be computed, as explained above, or one or more alternative measures may be computed.

As shown at step 310, the one or more measures may be compared against respective reference values to determine a status of the root canal, such as whether or not the root canal wall (dentin) is sufficiently clear of debris and/or sufficiently healthy (e.g. free from demineralization, caries and/or cracks). For example, one or more measures and associated reference values may be employed to determine whether or not debris (e.g. pulp tissue or other residue) is present on the root canal inner wall. One or more measures and associated reference values additionally or alternatively be employed to determine that the root canal is healthy or exhibits features such as demineralization, caries, and/or cracks. The reference values may be determined, for example, based on measurements previously made on healthy root canal tissue. One or more reference values may also be determined based on measurements previously made on root canals having demineralization, caries, cracks, and/or debris.

The measurement and processing of the measured signals may be repeated after performing a cleaning cycle (e.g. where cleaning is performed using one or more of various devices or tools, such as, but not limited to hand files, rotary instruments, irrigation with fluids, irrigation with ultrasonic or subsonic waves, diamond drills or stainless steel drills such as Gates Glidden burs) and the cleaning cycles and measurements may be repeated until it is deemed that the root canal is sufficiently clear of debris and/or sufficiently healthy, as shown at 315 in FIG. 4D.

Referring now to FIG. 4E, an example is provided in which measures of the status of dental tissue are calculated based on the processing of the amplitude and phase of photothermal and luminescence signals. As shown at "test 3", an example determination (estimation) of the presence or absence of debris at the surface associated with a dental tissue surface (such as, but not limited to, an inner surface of a root canal, a surface exposed while drilling but prior to reaching the pulp chamber and a surface of the pulp chamber) may be determined based on the phase of the modulated luminescence signal. For example, such a measure may be determined by comparing the measured luminescence phase to a reference phase (shown as Ref B in FIG. 4E). In one example implementation, a determination of the presence of debris may be made when the difference between measured luminescence phase and a reference luminescence phase exceeds a reference value. For example, the reference value may be 0.5°, 0.75°, 1°, 1.25° or 1.5°.

An example determination of the health status of dental tissue may be determined, as shown at "test 1", by comparing a first ratio generated at least in part based on the measured photothermal amplitude divided by the standard deviation of the photothermal amplitude, and a second ratio based at least in part on the measured photothermal phase divided by the standard deviation of the photothermal phase to respective reference values (shown as A1 and P1). A second determination of the health status of dental tissue, shown as "test 2", may be made by comparing the first and second ratios to additional respective reference values (shown as A2 and P2). The reference values may be selected such that:

(i) if either condition of test 2 fails, then the dental tissue interrogated by the intraoral probe is estimated to be healthy;

(ii) if either condition of test 1 fails and both conditions of test 2 pass, then it is estimated that early demineralization, caries and/or cracks may be present; and (iii) if both conditions of test 1 and test 2 pass, then it is estimated that advanced (e.g. more severe than in (ii) above) demineralization, caries and/or cracks may be present.

An example implementation involving tests 1, 2 and 3 is shown in FIG. 4F. After having performed a series of photothermal and luminescence measurements (e.g. at an internal tooth surface), the measurement may optionally be verified, as shown as "Valid Measurement?". For example, one or more tests may be performed to assess the relative strength of detected signals in order to determine whether or not the signals are indicative of a measurement of dental tissue. For example, one or more statistical measures may be determined in order to determine the presence or absence of a signal corresponding to a measurement of dental tissue. In one example implementation, a measurement error involving the standard deviation of one or more measures obtained from one or more signals (e.g. one or more of photothermal amplitude, photothermal phase, luminescence amplitude and luminescence phase) may be computed and compared with pre-selected reference error value. A non-limiting example error measure is shown in FIG. 4E. For example, during the process of scanning with an intraoral optical probe, an error measure (such as that shown in FIG. 4E) may be employed to validate the stability of the probe. If the measured error is larger than a pre-determined cut-off value, then the user may be alerted (e.g. instructed to repeat the scanning). The verification step may be particularly beneficial in endodontic applications to ensure that the distal elongate waveguide of an intraoral optical probe is making stable contact with the root canal wall (or another internal dental tissue surface), because unlike measurements performed on outer enamel surfaces, the contact of a probe with an internal dental surface cannot be visually confirmed by a test operator.

Referring again to FIG. 4F, test 3 may be employed to estimate whether or not debris is present at the dental tissue surface interrogated by the intraoral optical probe. This test may be combined with tests 1 and 2, as shown in the figure, to provide estimates of the status of the dental tissue as well as an estimate of the presence or absence of debris.

An example of the joint use of tests 1, 2 and 3 is also shown in FIG. 4F, where different outputs (2A, 2B, 3A, 3B, 4A and 4B) are associated with combinations of different outcomes of tests 1, 2 and 3. For example, output 3A or 4A may indicate the absence of soft debris (like bio films) on the wall surface (providing an estimate that the internal surface is a clean wall surface, where outcome 4A is more severe than that of outcome 3A. However, in the case of outputs 3A or 4A, the photothermal (PTR) response was still stronger than a healthy dentin crystal structure, and the stronger PTR response may be indicative of demineralization on the wall structure (like white spots) or cracks (due to temporary drilling or permanent cracks) on the dentin wall.

Outcomes 3B and 4B are indicative of the presence of debris (e.g. soft debris) on the dental tissue surface, and a clinician may elect to remove the soft debris first. However, as can be seen from FIG. 4F, outcomes 3B and 4B indicated that caries, demineralization and/or cracks may be present on the wall structures underneath the soft debris. After cleaning the wall surface to remove the soft debris, in the next scan, a clinician may determine, based on a subsequent measurement, whether or not demineralization and/or cracks are still be present on the crystal structure of the wall.

Figures 4H, 4I, 4J:
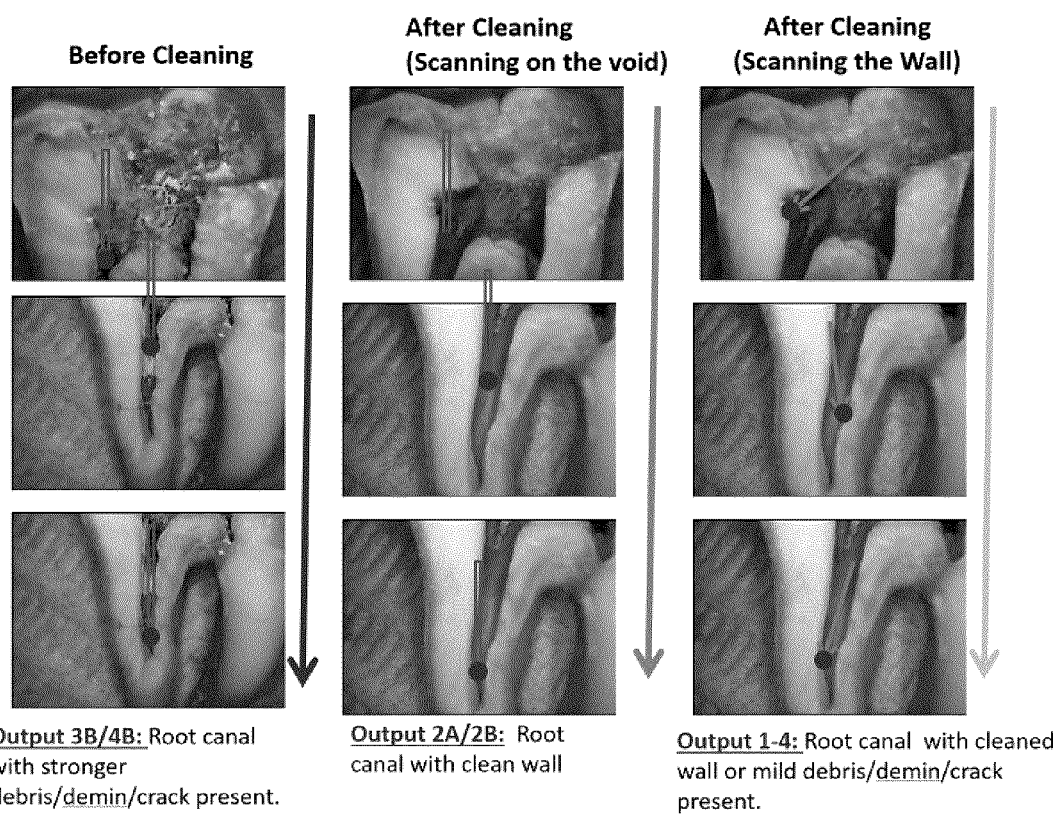
Figure 5G:
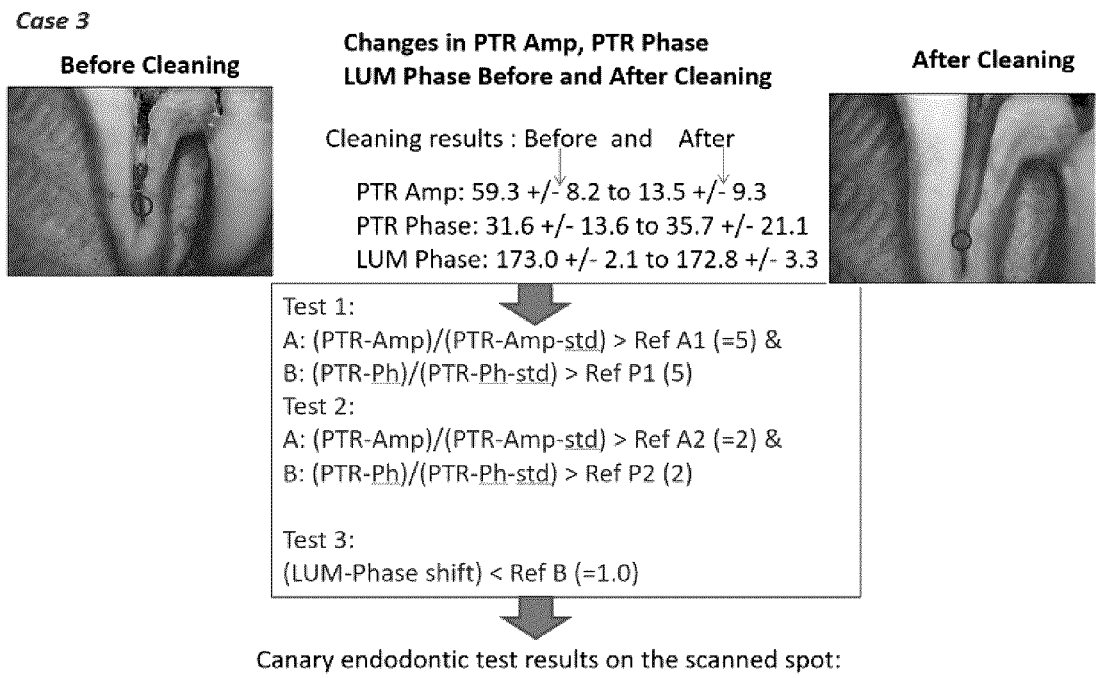
Figure 5J:
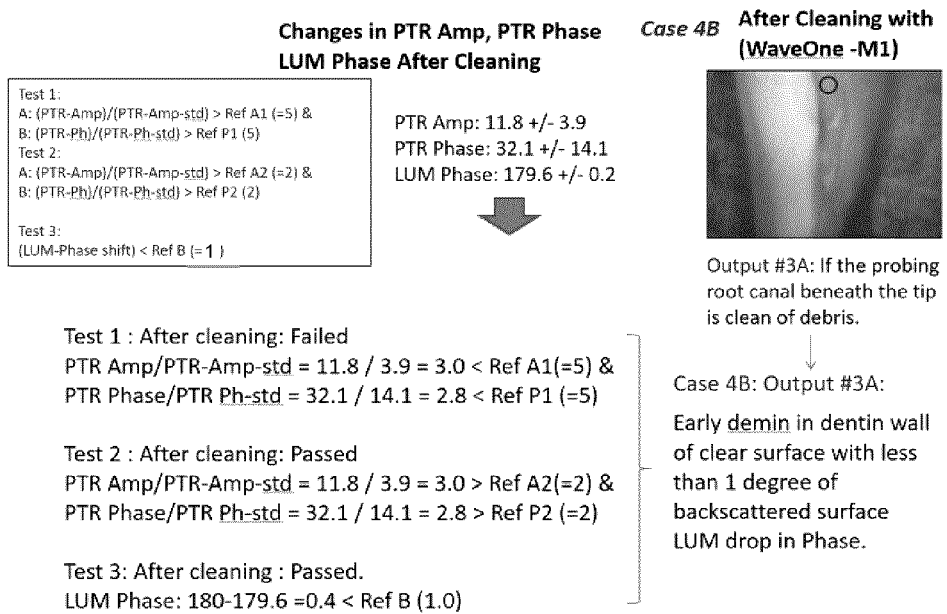
Figure 5K:
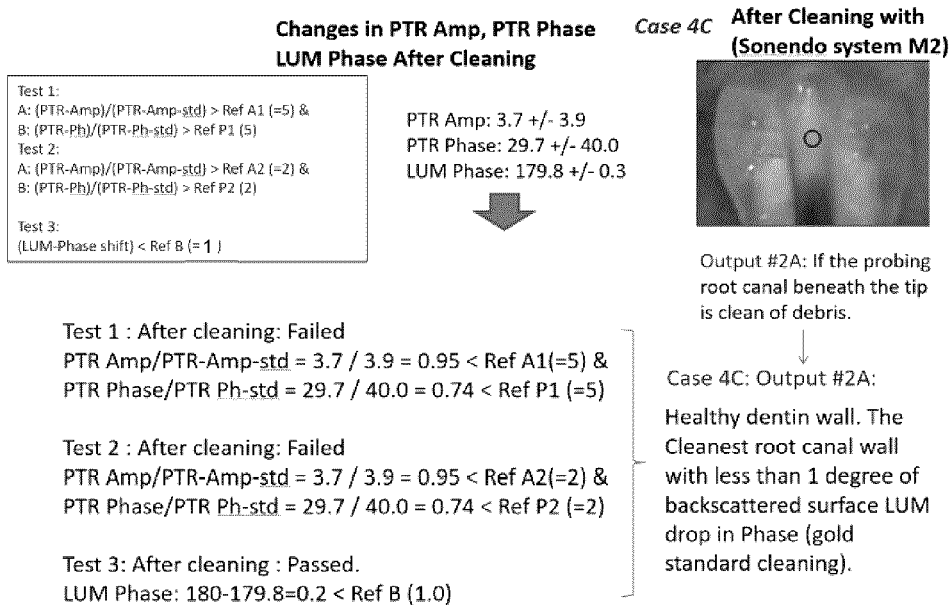
Figure 5L:
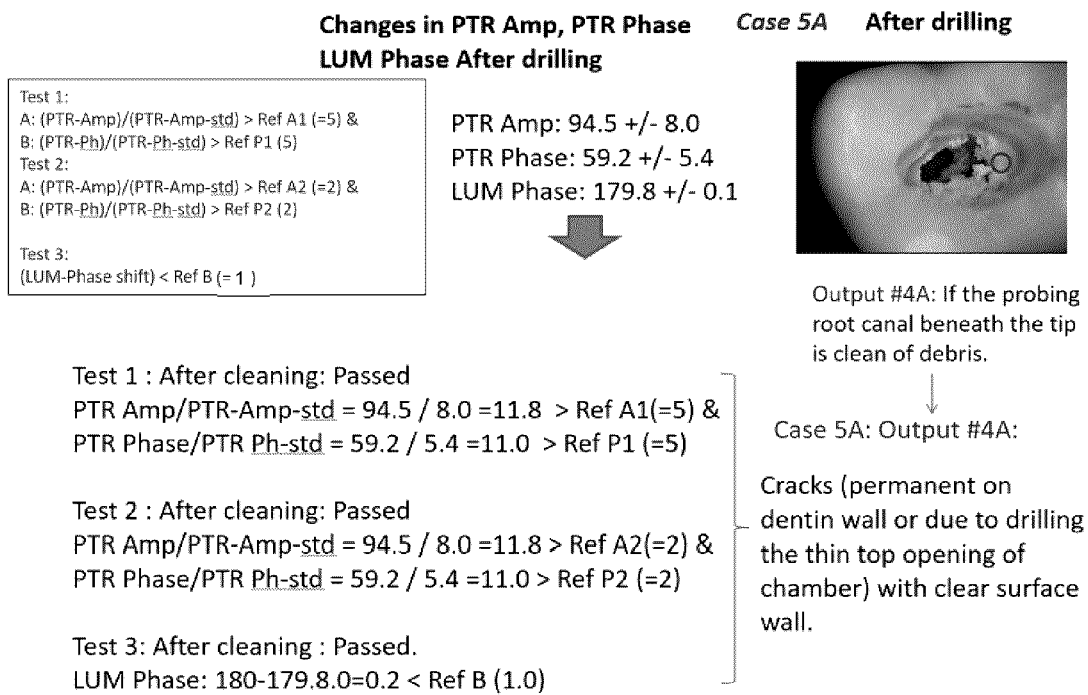
Figure 6A:
Figure 6B:
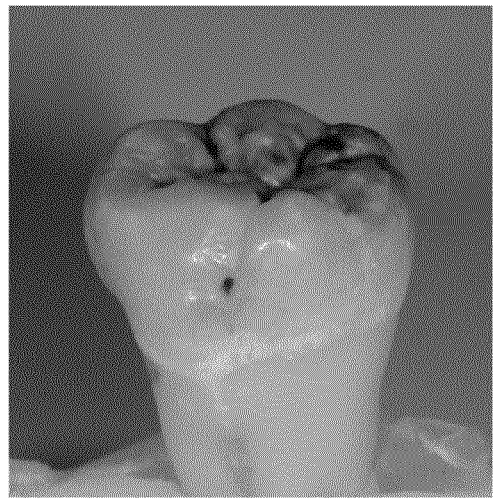
Figure 6C:
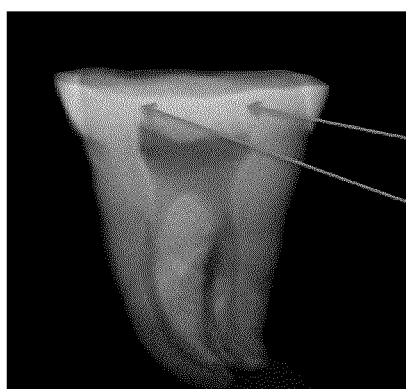
Figure 6C:
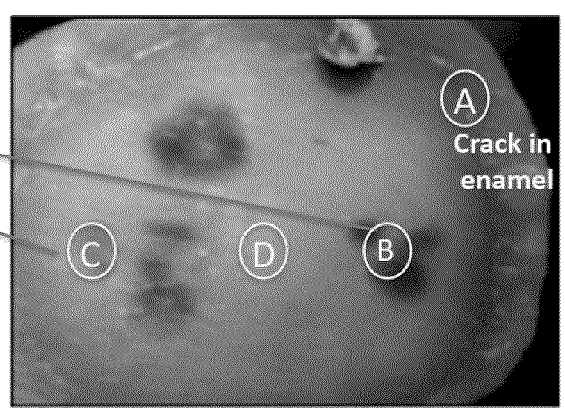
Figure 6F:
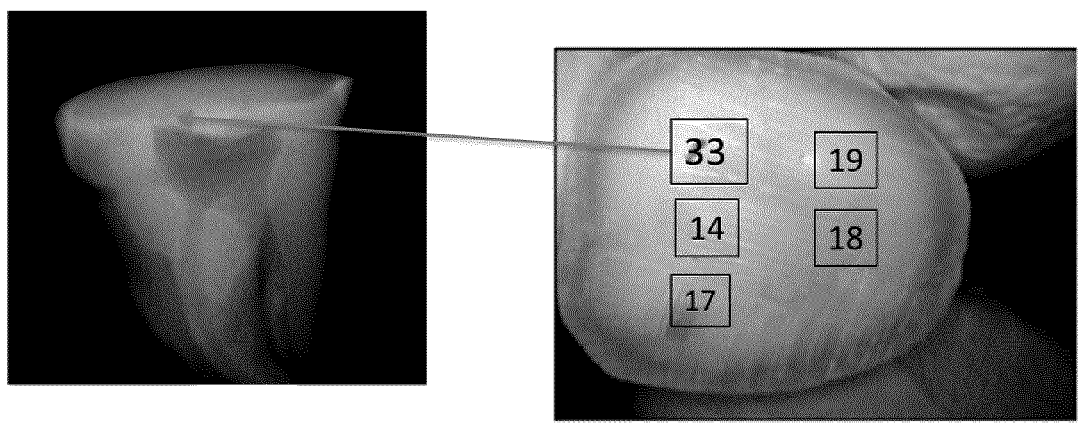
Figure 6F:
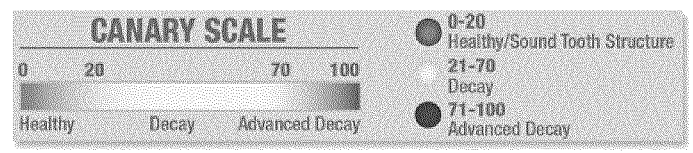

FIG. 4G illustrates different treatment steps that may be taken based on different possible outcomes of tests 1, 2 and 3, and the expected results of the combined tests after performing different treatments. FIG. 4H provides another example involving the use of intraoperative intraoral photothermal and luminescence measurements to detect the status of an internal dental tissue surface, and the intraoperative tracking of the effect of a cleaning step of the status of the internal dental tissue. For example, after removing the soft debris, outcome 3B might revert to outcome 3A or 2A or 2B in a subsequent measurement, while ideally, the outcome should shift to outcome 2A if the treatment was effective. In another example, after removing the soft debris, outcome 4B may revert to outcome 4A or 3A or 3B or 2A or 2B in a subsequent measurement, while ideally, the outcome should shift to outcome 2A if the treatment was effective.

FIGS. 5A-5L illustrate examples of difference types of outputs that can be generated before and after cleaning during an endodontic procedure.

Although the preceding example embodiments have disclosed various applications involving measurements of the inner surfaces and or walls of a root canal, it will be understood that an intraoral optical probe may be employed in additional applications involving the assessment of other internal surfaces of teeth. Non-limiting examples described in further detail below include measurements facilitating the location of the pulp chamber when initiating the root canal procedure (e.g. when entering the pulp chamber or inside of the clinical crown, examining the interior to detect cracks that have progressed from the exterior of the tooth surface), measurements facilitating the location of the entrance or orifice of one or more root canals from the pulp chamber, and measurements facilitating the detection of the apex or tip of a root canal.

For example, an intraoral optical probe may be employed to determine whether or not there may be any lateral canals before and/or after performing a cleaning procedure. This may be performed, for example, by performing measurements along the root canal walls. Elevated measurements (e.g. differing from one or more reference values) of the Canary Number (or another measure derived from photothermal and luminescence measurements) limited to this one location would indicate the presence of a lateral canal. This canal entrance or orifice may be small, for example with a diameter of approximately 0.2 mm.

Pulp Chamber Detection

In another example embodiment, an intraoral optical probe may be employed for endodontic procedure verification by determining the location of the pulp chamber prior to exposing the pulp chamber and the root canal.

There are sometimes challenges in locating either the pulp chamber or some of the root canals in teeth. Both pulp chambers and root canals can calcify over time, especially if exposed to either long term occlusal or bite loading or slowly progressing caries. In both situations, the pulp chamber or root canal will calcify in response to these situations. The calcification may not be as well organized as when the tooth is formed. Visually the tissue will appear as the same colour as the surrounding tissue and even with magnification one cannot find either the pulp chamber or entrance to the root canals. When attempting to find the pulp chamber in such a case, one typically slowly removes tooth structure in the area, looking for defects in the floor. Unfortunately, this approach can, in some case, lead to perforation of either the walls or floor of the root canal system. An improved method for detecting the location of the pulp chamber is therefore needed.

In some example embodiments, the location of the pulp chamber may be determined, for example, using a probe that employs a photothermal and luminescence detection modality, as follows. An initial entrance or access hole is first made into either the biting or occlusal surface of the tooth or into the lingual surface of anterior teeth. The position and orientation of the initial entrance or access hole may be determined, for example, based on radiographs and using knowledge of the standard or usual position for the pulp chamber. The access hole is drilled or prepared which creates micro-fractures in the root canal chamber, removing enamel and dentin in the access cavity preparation.

The elongate optical waveguide of the intraoral optical probe may be intermittently inserted into the access hole one or more times during the preparation of the access hole (i.e. stopping the drilling procedure and inserting the distal portion of the elongate optical waveguide into the access hole) and measurements are made. The photothermal and luminescence measurements are then compared to reference values, e.g. as described above with reference to FIGS. 4D and 4F.

An area residing over the pulp chamber will have associated photothermal and luminescence measurements that are different from healthy or carious dentin since there is a "hollow space" or pulp chamber beneath it. As the access hole approaches the pulp chamber, the intraoral optical probe may therefore be employed to provide measurements indicating the position and distance to the pulp chamber.

For example, as illustrated below in FIGS. 6A-6H, if an access hole is optically interrogated using an intraoral optical probe, then if the suspected area is very thin on a dentin wall without any soft debris due to drilling and the access hole is sufficiently proximal to the pulp chamber such that the pulp chamber will be opened through further drilling of the access hole, then the expected output is "4A" according to the example detection modality illustrated in FIG. 4E. However, if the suspected area wall is very thin on a dentin wall with soft debris due to drilling and the access hole is sufficiently proximal to the pulp chamber such that the pulp chamber will be opened through further drilling of the access hole, then the expected output is "4B". If the output determined through measurements made in an access hole is 3A or 3B, then the access hole is not sufficiently proximal to the pulp chamber to be readily opened and further drilling of the access hole should be performed to bring the access hole proximal to the pulp chamber. If the output determined through measurements made in an access hole is 2A or 2B then the access hole is not sufficiently proximal to the pulp chamber to be readily opened and further drilling of the access hole should be performed to bring the access hole proximal to the pulp chamber, where the amount of additional drilling needed is greater than that which would be required if the output were 3A or 3B.

In another example embodiment, the Canary Number may be employed to detect the presence of the pulp chamber below an access hole by scanning the floor of the preparation as one sequentially removed dentin. An elevated Canary Number 25 indicates that there is a void beneath the area. If the preparation is within the upper two thirds of the crown, then it may be determined that one is approaching the pulp chamber.

Figure 7A:
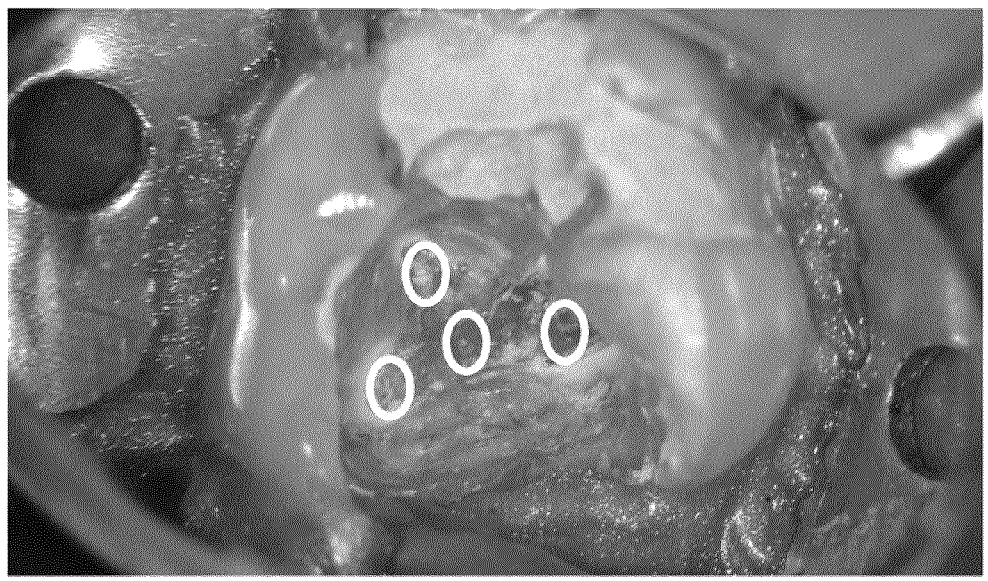
FIGS. 7A and 7B illustrate the use of an intraoral optical probe for the detection of the location of the pulp chamber.
Figure 7B:
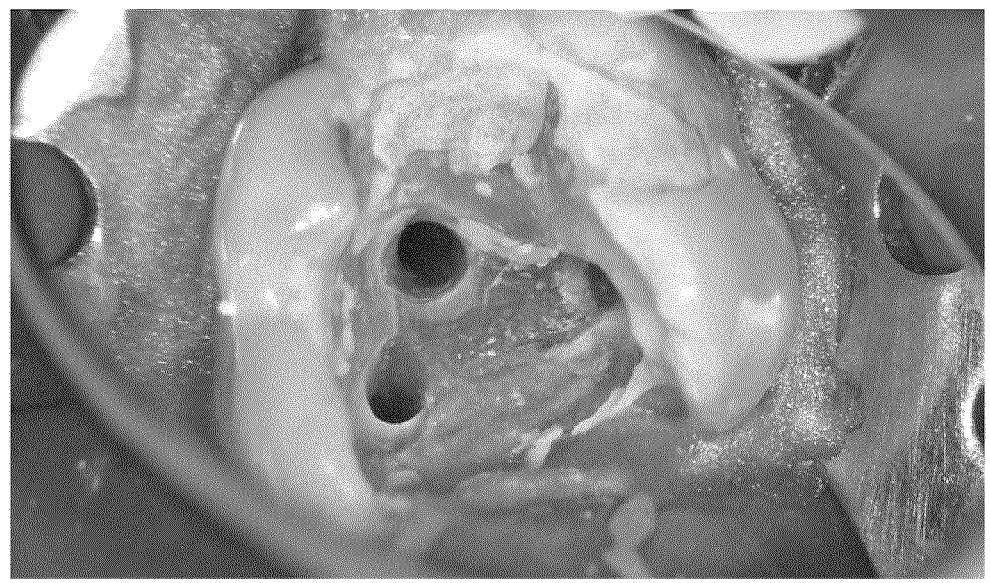
Figure 8A:
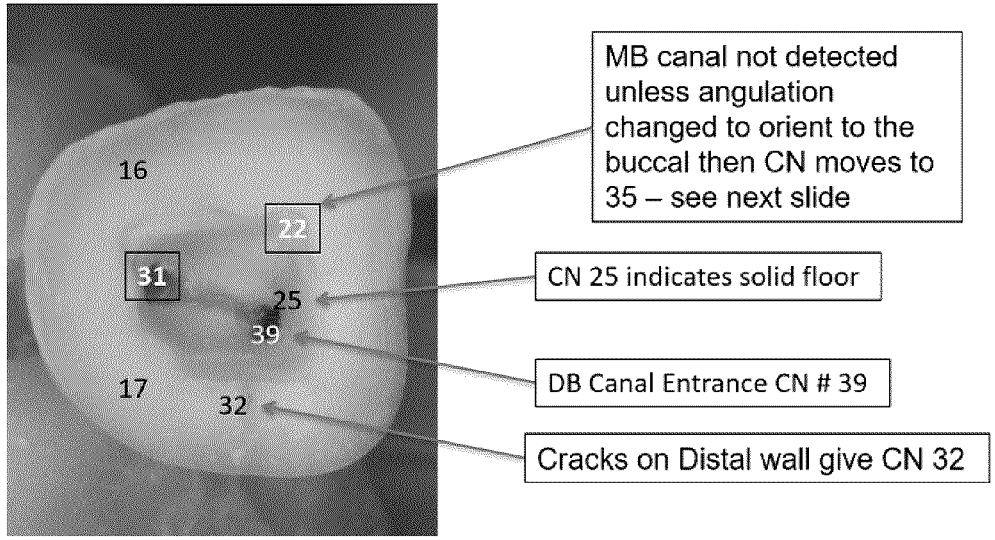
FIGS. 8A-8D illustrate an example method of detecting the presence additional root canals based on measurements made at the bottom surface of the pulp chamber.
Figure 8B:
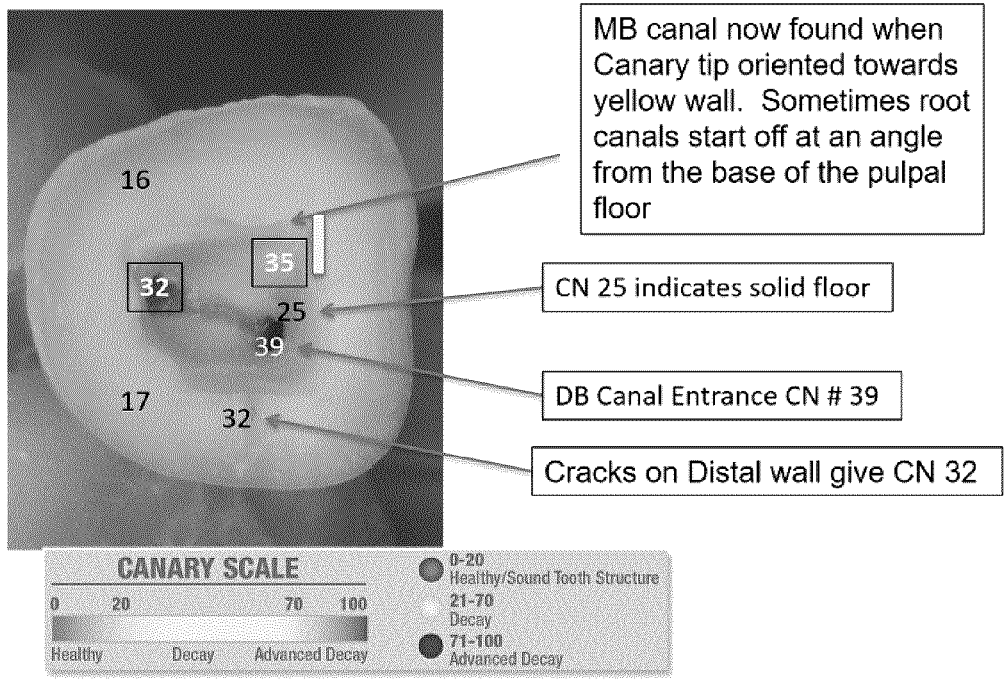
Figure 8C:
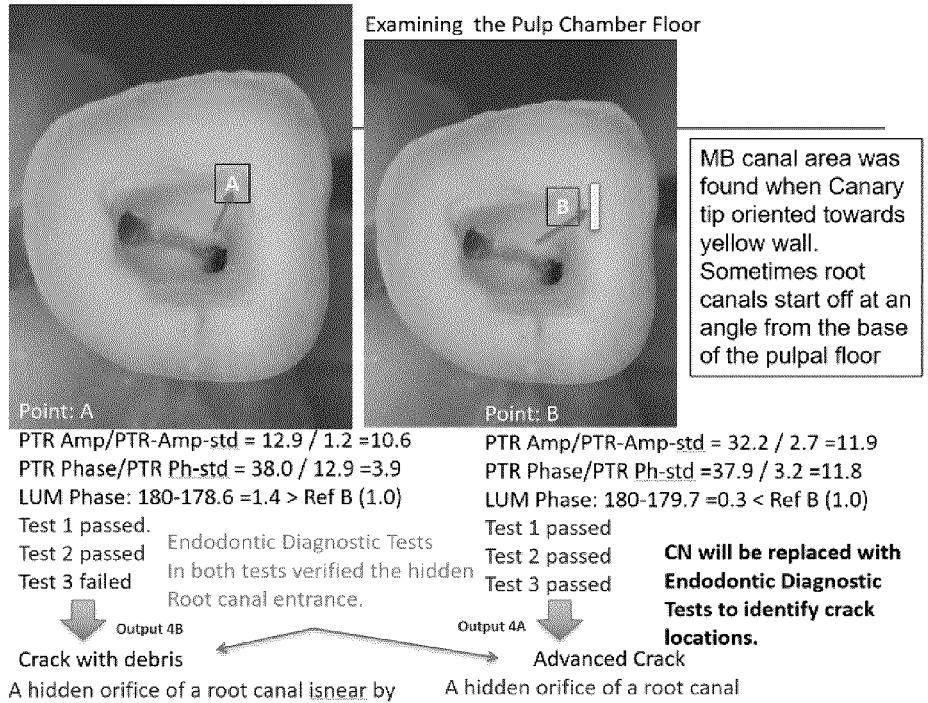
Figure 8D:
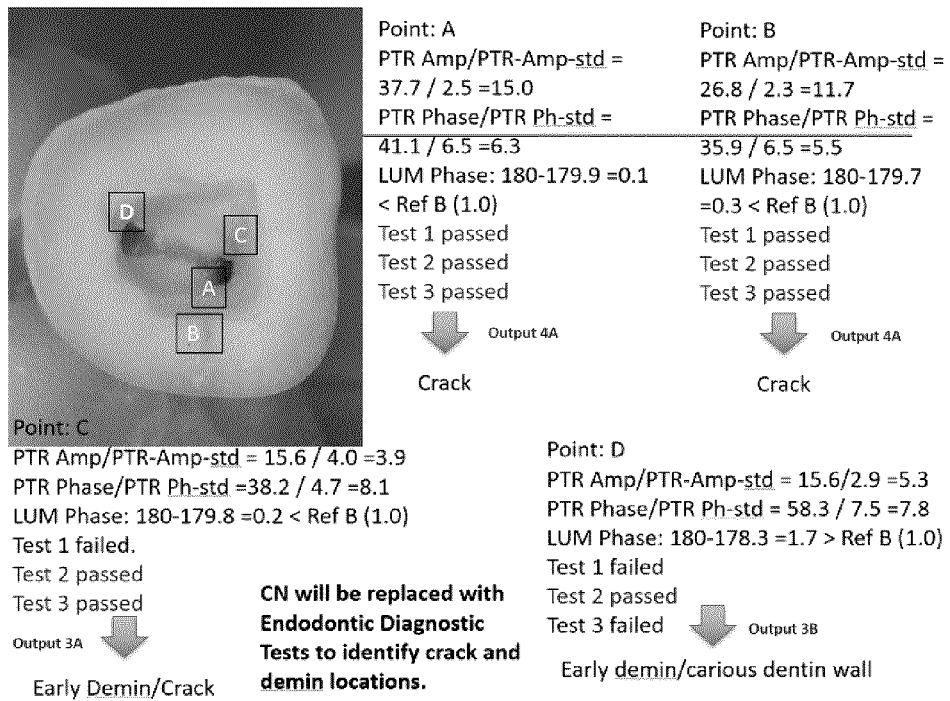

FIGS. 7A and 7B illustrate an example implementation of the use of an intraoral optical probe to perform photothermal and luminescence measurements for the detection of the pulp chamber. In FIG. 7A, the white circles indicate regions that are locally interrogated with an intraoral optical probe in order to detect the presence of the underlying pulp chamber. FIG. 7B shows the pulp chamber root removed and the location of the three root canal orifices.

Root Canal Detection from Pulp Chamber

In another example embodiment, an intraoral optical probe may be employed during an endodontic procedure, before and/or after performing a cleaning procedure, to detect the entrances or orifices to root canals that may not have been seen or could be detected with conventional methods, by examining the floor of the pulp chamber. This may be performed, for example, in the example case of a probe that employs a photothermal and luminescence detection modality, as follows. Once the pulpal floor has been located, the distal end of the elongate optical waveguide of the intraoral optical probe is inserted into the pulp chamber and measurements taken at a plurality of locations, including locations where root canal orifices are expected to be located based on typical anatomy. If the photothermal and luminescence measurements (e.g. the Canary Number or another measure derived from photothermal and luminescence measurements) is elevated (e.g. differing from one or more reference values) at a given location, then a determination may be made that a root canal orifice may reside proximal to the location. The orientation of the intraoral optical probe corresponding to the elevated measurement may be employed to infer an angle or direction associated with the extension of the additional root canal below the pulp chamber floor. A small bur or instrument may then be employed to initiate the opening of the root canal orifice. In some example implementations, the intraoral optical probe may be angled at different inclinations at a given location in order to probe (interrogate) the presence of root canals that extend in plurality of possible directions.

For example, the distal end of the intraoral optical probe may initially be angled initially at 90 degrees to the pulp chamber floor for the collection of photothermal and luminescence measurements. If the initial measurements are not sufficiently elevated (e.g. differing from one or more reference values), then the intraoral optical probe may be angled and additional measurements may be taken and processed to search for root canals extending in other directions. The determination of the presence or absence of an additional root canal may be based, for example, on the severity of an inferred crack (caused due to drilling), which can be employed as a guide to detect the hidden orifice of a root canal on the floor of the pulp chamber. For example, if one is scanning the floor of the pulp chamber and Canary Number is ≥30, then a determination may be made that the location of the elevated reading is associated with the presence of an orifice for a root canal.

Examples of the detection of additional root canals based on photothermal and luminescence measurements performed on dental tissue at the bottom surface of the pulp chamber are shown in FIGS. 8A-8D.

Root Canal Apex Detection

In another example embodiment, an intraoral optical probe may be employed for endodontic procedure verification by determining where the tips of the roots or apices are located and their associated lengths from the entrance cavity before and/or after performing a cleaning procedure.

The tooth is suspended by periodontal ligaments in the alveolar bone of the upper (maxillary) or lower (mandibular) jaw. The root canal will typically narrow and the walls become thinner as one approaches the apex or tip of the root canal. Preliminary studies indicate that as one scans a canal that is free of debris, the photothermal and luminescence signals will change as the root canal apex is approached. For example, it has been observed that as the root canal apex is approached, the Canary Number will start to increase above 35, and will continue to increase as it approaches the apex or opening of the root canal.

Figure 9:
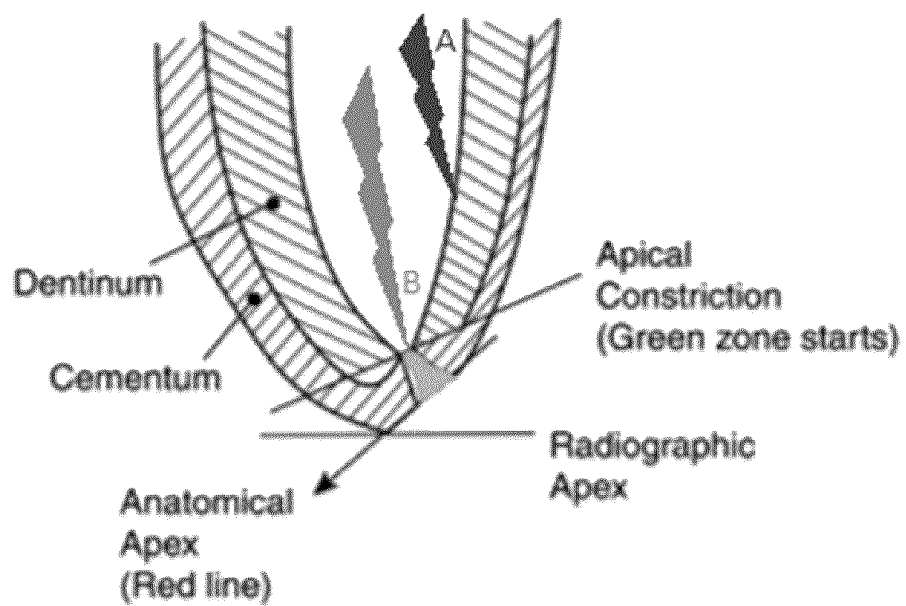
FIG. 9 illustrates an example embodiment involving the detection of a root canal apex using an intraoral optical probe.

Referring now to FIG. 9, a hollow wave-guide is shown making contact near the anatomical apex area of the root canal at Region B and making contact on the root canal wall at Region A. As noted above, once the root canal dentin wall is cleaned after removing the soft debris, the results obtained from performing tests 1, 2 and 3 (described above) would be expected to change from output 4B or 3B to output 2A or 2B. However, when a measurement is performed with the interrogating optical beam closer to the anatomical apex of the root canal, one would expect that the tests 1, 2 and 3 would produce result in output 2B instead of 2A, because in Region B, the scan spot would measure a drop in the luminesce phase due to a drop in the backscattering light from the void or soft tissue area of the anatomical apex (i.e. with test 2 and test 3 failing). In addition to output 2B being obtained measured at point B, one would expect that a repeated measurement error value $E_i$ at Region B would be above a cutoff value $E_{apex}$, where $E_{cutoff} > E_i > E_{apex}$. The measurement errors $E_{cutoff}$ and $E_{apex}$ may be determined from the clinical measurements, while the measurement error $E_i$ is defined as follows:

$$E_i = \sqrt{\left(\frac{PTR_{Amp}STD}{PTR_{Amp}}\right)^2 + \left(\frac{PTR_{Phase}STD}{PTR_{Phase}}\right)^2 + \left(\frac{LUM_{Amp}STD}{LUM_{Amp}}\right)^2 + \left(\frac{LUM_{Phase}STD}{LUM_{Phase}}\right)^2}.$$

Using these example testing scenarios, an anatomical apex of region of the root canal may be detected using an intraoral probe having a distal hollow waveguide.

Accordingly, in one example embodiment, the tip (apex) of a root canal or opening into the bone of the jaw could be identified by extending the distal end of the intraoral optical probe into the root canal and monitoring the detected photothermal and luminesce measurements to detect one or more measurement values that are indicative of the presence of surrounding bone and vascular tissue at the apex of the root canal.

In one example embodiment, an intraoral optical probe may be employed to provide a measure of the length of the root canal system. In one example implementation, the elongate optical waveguide of the intraoral optical probe is inserted into the root canal and optical measurements are recorded by the probe as the distal end of the elongate optical waveguide is translated relative to the root canal. Once the distal end of the root canal (the tip or orifice of the root canal) is reached (e.g. according to the method described above), a measurement of the length of the root canal may be obtained from a graduated scale provided on the elongate optical waveguide.

Although many of the preceding example embodiments were presented in the example context of endodontic procedures, it will be understood that the example devices, systems and methods described herein may be applied to a wide variety of dental procedures. For example, the example intraoral optical probes and methods of use thereof disclosed herein may be adapted to facilitate the internal characterization of a variety of internal structures of a tooth, both natural and artificial (e.g. internal features formed during restorative procedures). For example, the example intraoral optical probes and methods of use thereof disclosed above may be adapted to facilitate the internal characterization of the interior of a cavity prior to filling the cavity. It will be understood that the present example embodiments may be applied dental procedures including, but not limited to, examining the walls and floor of cavity preparation, examining the tooth structure after preparation for partial or full coverage crowns, examining the pits and fissures after preparation for a conservative or preventive resin cavity preparation. These examinations would be used to detect the status of the tooth structure including enamel and dentin to confirm that no caries or demineralized tissue remains, to determine how close the base of the cavity preparation is to the pulp chamber or root canal system, to detect cracks on the walls or floor of the cavity preparation, to examine the margins of the restorative materials to ensure that no caries or demineralized tissue is present or remains after preparation.

In some example embodiments, during a cavity preparation or preparation another type of dental restorative procedure, an intraoral optical probe having a distal elongate optical waveguide may be employed to determine whether or not the dentin within an internal portion of the tooth (e.g. within a cavity) is healthy or diseased. Such measurements pertaining to the status of internal dental tissue could be employed to provide an operator with feedback that may be employed to inform decisions regarding when and how to continue with treatment of the tooth. For example, the present inventors have found that when an intraoral optical probe having a distal elongate optical waveguide is employed that is capable of performing photothermal and luminescence measurements, the photothermal and luminescence signals change as caries dentin is removed from the interior of a cavity preparation. For example, in the case of the Canary Number (defined above), it has been found that the Canary Number decreases and moves closer to a value of 20 (using a frequency of 2 Hz).

Figure 10:
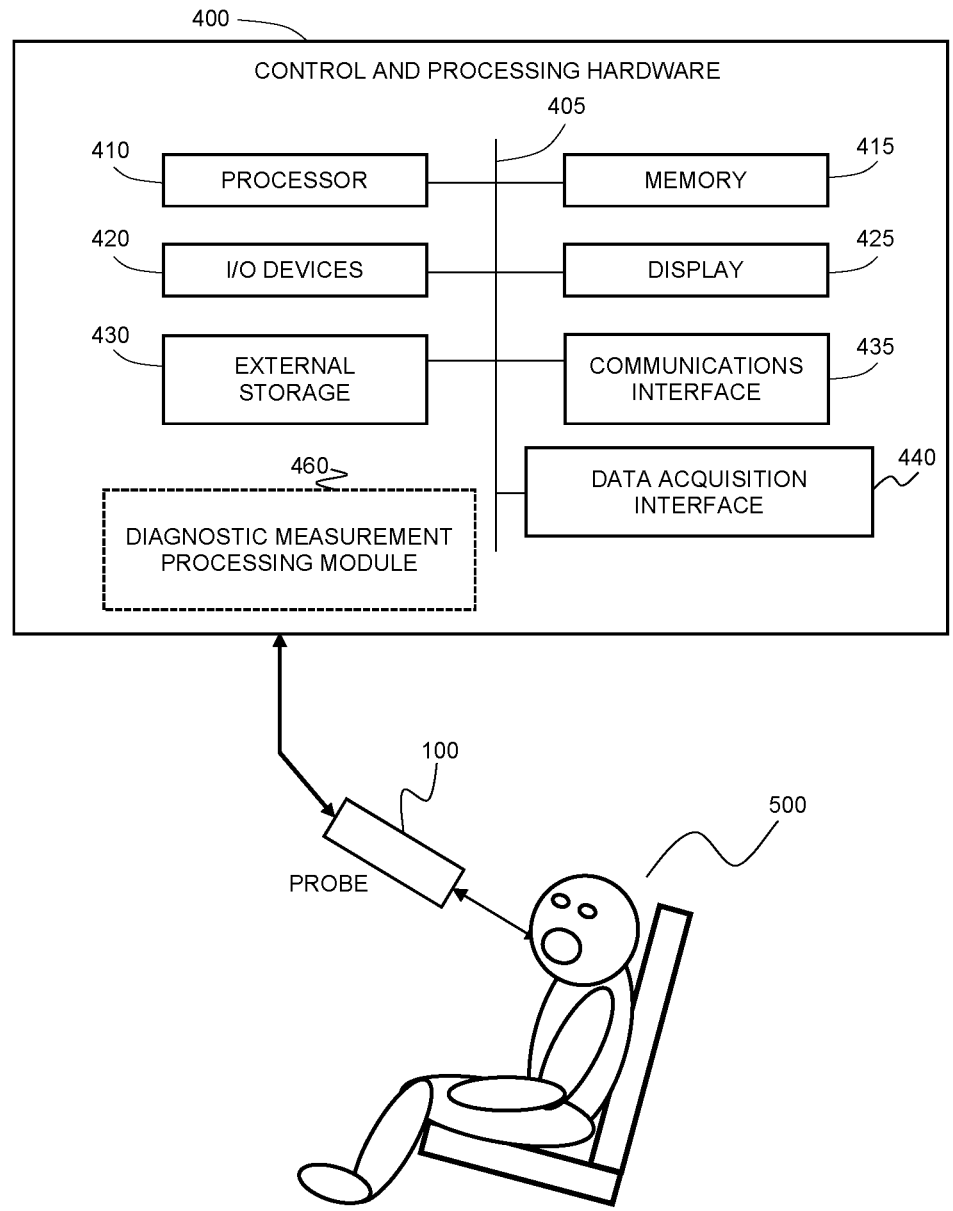
FIG. 10 illustrates an example system for performing intraoral optical measurements to verifying different stages of an endodontic procedure.

Referring now to FIG. 10 an example system is shown for performing diagnostic measurements with an intraoral optical probe according to the example embodiments disclosed above. The example system includes an intraoral optical probe 100 that is operatively coupled to a control and processing unit 400. The intraoral optical probe 100 may be based, for example, on the example intraoral optical probe embodiments shown in FIG. 2A or 2B, or alternative intraoral optical probe configurations such as those described above or variations thereof.

As shown in the example embodiment illustrated in FIG. 10, control and processing hardware 400 may include a processor 410, a memory 415, a system bus 405, one or more input/output devices 420, and a plurality of optional additional devices such as communications interface 435, display 425, external storage 430, and data acquisition interface 440. The control and processing hardware 400 may include and execute instructions for processing diagnostic measurements made by the diagnostic detection subsystem of probe 100, for example, in process the signals detected by the intraoral optical probe, as represented by diagnostic measurement processing module 460.

Some aspects of the methods described herein can be partially implemented via hardware logic in processor 410 and partially using the instructions stored in memory 415. Some embodiments may be implemented using processor 410 without additional instructions stored in memory 415. Some embodiments are implemented using the instructions stored in memory 415 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 400 may be provided as an external component that is interfaced to a processing device. For example, one or more components of the control and processing hardware 400 may be provided within probe 100.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Modification of the Canary System® with Distal Elongate Optical Waveguide for Optical Interrogation of Tissue within a Root Canal Referring now to FIGS. 11A-11D, a series of photographs are provided that show the modification of an existing Canary System® intraoral optical probe with the addition of an elongate optical waveguide for performing internal optical measurements of dental tissues.

FIG. 11A shows the distal region of the handheld intraoral optical probe 600 having a hollow elongate optical waveguide 605 extending therefrom. The specifications of the hollow waveguide were as follows: internal diameter=1500

μm, typical Loss=0.1 dB/m, Output divergence ½ Angle=30 mRad, minimum bend radius=3 cm, maximum power=10 W.

As can be seen in FIGS. 11A and 11B, the hollow elongate optical waveguide 605 was secured to the handheld intraoral optical probe body 600 via a plastic sleeve 610. The hollow plastic elongate optical waveguide 605 was secured to the plastic sleeve 610. Curing light based dental sealant material was used to firm the plastic tip-plastic hollow waveguide joint. Point laser output of the Canary system was used to confirm the alignment during the polymerization of the sealant material. FIGS. 11C and 11D show lateral and axial view of the elongate optical waveguide 605 secured to the probe body via the plastic sleeve 610.

As shown in FIGS. 11E and 11F, the distal portion of the elongate optical waveguide 605 was inserted, ex vivo, into an exposed root canal of a tooth 620. FIG. 11E shows a photograph in which the elongate optical waveguide inserted into the root canal such that the distal end of the elongate optical waveguide resides part way along the length of the root canal. FIG. 11F shows a photograph in which the elongate optical waveguide resides near the distal region of the root canal (remote from the tooth surface), and a bright region can be seen near the base of the tooth. This bright region is caused by the optical scattering of laser light delivered by the distal end of the elongate optical waveguide.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of optically interrogating an interior region of a tooth using an intraoral probe, the intraoral probe comprising:
   a body suitable for use in a handheld configuration;
   a modulated light source housed within the body, wherein the modulated light source is configured to generate incident modulated optical energy;
   an elongate optical waveguide extending from a distal region of the body, wherein the elongate optical waveguide is in optical communication with the modulated light source;
   a first optical detector configured to detect luminescence energy; and
   a second optical detector configured to detect photothermal energy;
   the method comprising:
      after inserting the elongate optical waveguide into the interior region of the tooth, employing the intraoral probe to deliver the incident modulated optical energy onto dental tissue within the interior region of the tooth and performing luminescence and photothermal measurements at a plurality of locations by:
         collecting the luminescence energy responsively emitted from the dental tissue and detecting luminescence signals with the first optical detector;
         collecting the photothermal energy responsively emitted from the dental tissue and detecting photothermal signals with the second optical detector; and
      processing the luminescence signals and the photothermal signals to determine one or more measures; and
      comparing the one or more measures to reference values to identify a presence of one or more of debris, cracks, a pulp chamber residing beneath the dental tissue, and an unexposed root canal on the floor of the pulp chamber.

2. The method according to claim 1 wherein the one or more measures are employed to determine, from the plurality of locations, a location corresponding to the unexposed root canal or the pulp chamber.

3. The method according to claim 2 wherein an orientation of the intraoral probe when collecting the luminescence energy and the photothermal energy at the location corresponding to the unexposed root canal is employed to determine a direction associated with the unexposed root canal.

4. The method according to claim 3 wherein the orientation of the intraoral probe is varied while collecting the photothermal energy and the luminescence energy at one or more of the plurality of locations, thereby facilitating the detection of unexposed root canals extending in a plurality of directions.

5. The method according to claim 1 wherein the presence of debris is determined, at least in part, based on a comparison between a luminescence phase and a pre-determined phase value.

6. The method according to claim 1 wherein the following steps are performed prior to determining the one or more measures:
   processing the luminescence signals to calculate a measurement error based, at least in part, on a ratio comprising a standard deviation of a luminescence phase divided by an average luminescence phase; and
   comparing the measurement error to a threshold error to determine whether or not the luminescence signals correspond to valid measurements.

7. The method according to claim 1 wherein at least one of the one or more measures is generated, at least in part, based on:
   a first ratio comprising an average photothermal amplitude divided by a standard deviation of the photothermal amplitude; and
   a second ratio comprising an average photothermal phase divided by a standard deviation of the photothermal phase.

8. The method according to claim 7 wherein the determination of the presence of debris or the crack is determined, at least in part, based on:
   a comparison of the first ratio to a photothermal amplitude reference ratio; and
   a comparison of the second ratio to a photothermal phase reference ratio.

9. The method according to claim 8 when the photothermal amplitude reference ratio is a first photothermal amplitude reference ratio, and wherein the photothermal phase reference ratio is a first photothermal phase reference ratio, the method further comprising:
   determining a presence of healthy dental tissue when one or more of the following conditions are met:
      the first ratio is less than the first photothermal amplitude reference ratio and less than a second photothermal amplitude reference ratio; and
      the second ratio is less than the first photothermal phase reference ratio and less than a second photothermal phase reference ratio.

10. The method according to claim 8 when the photothermal amplitude reference ratio is a first photothermal amplitude reference ratio, and wherein the photothermal phase reference ratio is a first photothermal phase reference ratio, the method further comprising:
   determining a presence of one or both of demineralization and cracks when the first ratio is greater than the first photothermal amplitude reference ratio and the second ratio is greater than the first photothermal phase reference ratio, and at least one of the following conditions are met:
      the first ratio less than a second photothermal amplitude reference ratio; and
      the second ratio less than a second photothermal phase reference ratio.

11. The method according to claim 8 when the photothermal amplitude reference ratio is a first photothermal amplitude reference ratio, and wherein the photothermal phase reference ratio is a first photothermal phase reference ratio, the method further comprising:
   determining a presence of at least one of cracks, caries and demineralization when both of the following conditions are met:
      the first ratio is greater than the first photothermal amplitude reference ratio and greater than a second photothermal amplitude reference ratio; and
      the second ratio is greater than the first photothermal phase reference ratio and greater than a second photothermal phase reference ratio.

12. An intraoral optical system for performing assessment of an endodontic procedure or cavity preparations, said intraoral optical system comprising:
   a body suitable for use in a handheld configuration;
   a modulated light source housed within the body;
   an elongate optical waveguide extending from a distal region of the body, and wherein said elongate optical waveguide is in optical communication with said modulated light source for delivering incident modulated optical energy to dental tissue when said elongate optical waveguide is inserted into an interior region of a tooth and for collecting luminescence energy responsively emitted from the dental tissue;
   an optical detector capable of detecting the luminescence energy collected by said elongate optical waveguide; and
   processing circuitry operatively coupled to said modulated light source and said optical detector, wherein said processing circuitry comprises memory coupled with one or more processors to store instructions, which when executed by said one or more processors, causes said one or more processors to perform operations comprising:
      processing luminescence signals obtained from said optical detector to determine a luminescence phase associated with detected luminescence energy relative to a reference phase associated with said modulated light source; and
      employing the luminescence phase to detect a presence of debris on an internal surface associated with the dental tissue.

13. The intraoral optical system according to claim 12 wherein said optical detector is a first optical detector and wherein said elongate optical waveguide is further configured for collecting photothermal energy responsively emitted from the dental tissue;
   said intraoral optical system further comprising a second optical detector capable of detecting the photothermal energy collected by said elongate optical waveguide; and
   wherein said processing circuitry is further configured to perform operations comprising:
      processing photothermal signals obtained from said second optical detector to determine a photothermal amplitude associated with detected photothermal energy;
      processing the photothermal signals to determine a photothermal phase associated with detected photothermal energy relative to the reference phase associated with said modulated light source; and
      employing the photothermal amplitude and the photothermal phase to determine a health status of the dental tissue.

14. The intraoral optical system according to claim 12 wherein said elongate optical waveguide is flexible.

15. The intraoral optical system according to claim 12 wherein said elongate optical waveguide is a hollow optical waveguide.

16. The intraoral optical system according to claim 12 wherein said elongate optical waveguide comprises a hollow-core optical fiber having a reflective coating on a surface thereof.

17. The intraoral optical system according to claim 16 wherein at least a distal end of the hollow-core optical fiber is sealed.

18. The intraoral optical system according to claim 12 wherein said elongate optical waveguide is secured to the body by a distal support that is removably attachable to the body.

19. The intraoral optical system according to claim 12 wherein said modulated light source is modulated at a frequency of at least 15 Hz.

20. A method of detecting a root canal apex during an endodontic procedure using an intraoral probe, the intraoral probe comprising:
   a body suitable for use in a handheld configuration;
   a modulated light source housed within the body, wherein the modulated light source is configured to generate incident modulated optical energy;
   an elongate optical waveguide extending from a distal region of the body, wherein the elongate optical waveguide is in optical communication with the modulated light source;
   a first optical detector configured to detect luminescence energy; and
   a second optical detector configured to detect photothermal energy;
   the method comprising:
      after inserting the elongate optical waveguide into a root canal, employing the intraoral probe to deliver the incident modulated optical energy within the root canal;
      collecting the luminescence energy responsively emitted from the dental tissue and detecting luminescence signals with the first optical detector;
      collecting the photothermal energy responsively emitted from the dental tissue and detecting photothermal signals with the second optical detector; and processing the luminescence signals and the photothermal signals to determine when a distal region of the elongate optical waveguide is positioned proximal to the apex of the root canal.

* * * * *